United States Patent
White et al.

(10) Patent No.: US 10,415,027 B2
(45) Date of Patent: Sep. 17, 2019

(54) TREATMENT FOR AIRWAY CAST OBSTRUCTION

(71) Applicant: NATIONAL JEWISH HEALTH, Denver, CO (US)

(72) Inventors: Carl W. White, Denver, CO (US); Livia A. Veress, Denver, CO (US)

(73) Assignee: National Jewish Health, Denver, CO (US)

( * ) Notice: Subject to any disclaimer, the term of this patent is extended or adjusted under 35 U.S.C. 154(b) by 215 days.

(21) Appl. No.: 14/649,238

(22) PCT Filed: Dec. 5, 2013

(86) PCT No.: PCT/US2013/073372
§ 371 (c)(1),
(2) Date: Jun. 3, 2015

(87) PCT Pub. No.: WO2014/089327
PCT Pub. Date: Jun. 12, 2014

(65) Prior Publication Data
US 2015/0322421 A1    Nov. 12, 2015

Related U.S. Application Data

(60) Provisional application No. 61/733,798, filed on Dec. 5, 2012.

(51) Int. Cl.
| | | |
|---|---|---|
| C12N 9/72 | (2006.01) | |
| A61K 9/00 | (2006.01) | |
| A61K 38/48 | (2006.01) | |
| A61K 38/49 | (2006.01) | |

(52) U.S. Cl.
CPC .......... *C12N 9/6459* (2013.01); *A61K 9/0078* (2013.01); *A61K 38/49* (2013.01); *C12N 9/6462* (2013.01); *A61K 38/482* (2013.01); *C12Y 304/21068* (2013.01); *C12Y 304/21073* (2013.01)

(58) Field of Classification Search
CPC .. A61K 38/54; A61K 36/185; A61K 38/4826; A61K 38/4873; A61K 38/465; A61K 38/47; C12Q 1/37; G01N 33/6896; G01N 2800/52; G01N 2333/976; G01N 2800/2828; C12Y 304/21001; C12Y 304/22002; C12Y 301/01; C12Y 302/01; C12Y 304/00; C12Y 304/21004
See application file for complete search history.

(56) References Cited

U.S. PATENT DOCUMENTS

| 5,612,029 A | 3/1997 | Bennett et al. |
| 2005/0169908 A1 | 8/2005 | Murakami et al. |
| 2011/0070167 A1 | 3/2011 | Enkhbaatar et al. |

FOREIGN PATENT DOCUMENTS

WO    WO 2004/058186    7/2004

OTHER PUBLICATIONS

Allon et al. "Inhalation exposure to sulfur mustard in the guinea pig model: Clinical, biochemical and histopathological characterization of respiratory injuries," Toxicology and Applied Pharmacology, Dec. 2009, vol. 241, No. 2, pp. 154-162.
American College of Emergency Physicians and American Academy of Neurology "Clinical Policy: Use of Intravenous tPA for the Management of Acute Ischemic Stroke in the Emergency Department," Annals of Emergency Medicine, Feb. 2013, vol. 61, No. 2, pp. 225-243.
Anderson et al. "Pathologic Changes in Rat Lungs Following Acute Sulfur Mustard Inhalation," Inhalation Toxicology, 1996, vol. 8, pp. 285-297.
Balali-Mood et al. "Comparison of Early and Late Toxic Effects of Sulfur Mustard in Iranian Veterans," Basic & Clinical Pharmacology & Toxicology, Oct. 2006, vol. 99, No. 4, pp. 273-282.
Costello et al. "Treatment of plastic bronchitis in a Fontan patient with tissue plasminogegn activator: a case report and review of the literature." Pediatrics, Apr. 2002, vol. 109, No. 4, pp. e67.
Graham et al. "Historical perspective on effects and treatment of sulfur mustard injuries," Chemico-Biological Interactions, Dec. 2013, vol. 206, No. 3, pp. 512-522.
Heath et al. "Prospective, Longitudinal Study of Plastic Bronchitis Cast Pathology and Responsiveness to Tissue Plasminogen Activator (tPA)." Pediatric Cardiology, Dec. 2011, vol. 32, No. 8, pp. 1182-1189.
Jugg et al. "N-acetyl-L-cysteine protects against inhaled sulfur mustard poisoning in the large swine," Clinical Toxicology, May 2013, vol. 51, No. 4, pp. 216-224.
Rancourt et al. "Tissue factor pathway inhibitor prevents airway obstruction, respiratory failure and death due to sulfur mustard analog inhalation," Toxicology and Applied Pharmacology, Oct. 2013, vol. 272, No. 1, pp. 86-95.
Rancourt et al. "Airway tissue factor-dependent coagulation activity in response to sulfur mustard analog 2-chloroethyl ethyl sulfide," American Journal of Physiology Lung Cellular and Molecular Physiology, Jan. 2012, vol. 302, No. 1, pp. L82-L92.
Vadasz et al. "Update in Acute Lung Injury and Critical Care 2010," American Journal of Respiratory and Critical Care Medicine, May 2011, vol. 183, No. 9, pp. 1147-1152.
Veress et al. "Airway Obstruction Due to Broncial Vascular Injury after Sulfer Mustard Analog Inhalation." American Journal of Respiratory and Critical Care Medicine, 2010, vol. 182, No. 11, pp. 1352-1361.
Veress et al. "Tissue Plasminogen Activator Prevents Mortality from Sulfur Mustard Analog-Induced Airway Obstruction," American Journal of Respiratory Cell and Molecular Biology, Apr. 2013, vol. 48, No. 4, pp. 439-447.

(Continued)

*Primary Examiner* — Kade Ariani
(74) *Attorney, Agent, or Firm* — Sheridan Ross P.C.

(57) ABSTRACT

The present invention is directed to methods of treatment of airway obstruction associated with fibrin-containing cast formation by administering a fibrinolytic agent.

13 Claims, 24 Drawing Sheets

(56) References Cited

OTHER PUBLICATIONS

International Search Report and Written Opinion for International (PCT) Patent Application No. PCT/US13/73372, dated Apr. 15, 2014 10 pages.
International Preliminary Report on Patentability for International (PCT) Patent Application No. PCT/US2013/073372, dated Jun. 18, 2015 9 pages.
Database Biosis [Online] Biosciences Information Service, Philadelphia, PA, US; Apr. 2011, He Yan-Quing et al.: "Effects of urokinase in small dose on acute exacerbation of chronic obstructive pulmonary disease," Database accession No. PREV201100399835, 1 page, 2011.
Do et al. "Fontan Patient with Plastic Bronchitis Treated Successfully Using Aerosolized Tissue Plasminogen Activator: A Case Report and Review of the Literature," Pediatric Cardiology, 2009, vol. 30, No. 3, pp. 352-355.
Enkhbaatar et al. "Aerosolized Tissue Plasminogen Inhibitor Improves Pulmonary Function in Sheep with Burn and Smoke Inhalation," Shock, Jul. 2004, vol. 22, No. 1, pp. 70-75.
Gibb et al. "Management of Plastic Bronchitis With Topical Tissue-type Plasminogen Activator," Pediatrics, Aug. 2012, vol. 130, No. 2, pp. E446-E450.
Poursaleh et al. "Treatment for sulfur mustard lung injuries; new therapeutic approaches from acute to chronic phase," DARU Journal of Pharmaceutical Sciences, Sep. 2012, vol. 20, 27, 6 pages.
Wakeham et al. "Long-term treatment of plastic bronchitis with aerosolized tissue plasminogen activator in a Fontan patient," Pediatric Critical Care Medicine, Jan. 2005, vol. 6, No. 1, pp. 76-78.
Extended Search Report for European Patent Application No. 13859652.3, dated Jun. 7, 2016 9 pages.
Eberlein et al. "Plastic Bronchitis: A Management Challenge," The American Journal of the Medical Sciences, Feb. 2008, vol. 335, No. 2, pp. 163-169.

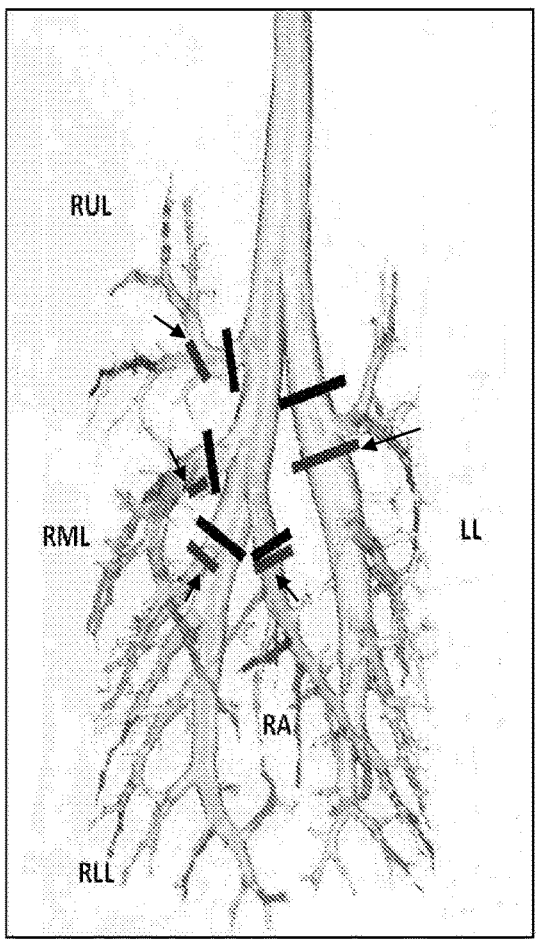
Fig. 1A
Fig. 1B
| % Occlusion | Cast Score |
|---|---|
| 0% | 0 |
| 1 - 14% | 1 |
| 15 - 29% | 2 |
| 30 - 49% | 3 |
| 50 - 64% | 4 |
| 65 - 79% | 5 |
| 80 - 99% | 6 |
| 100% | 7 |
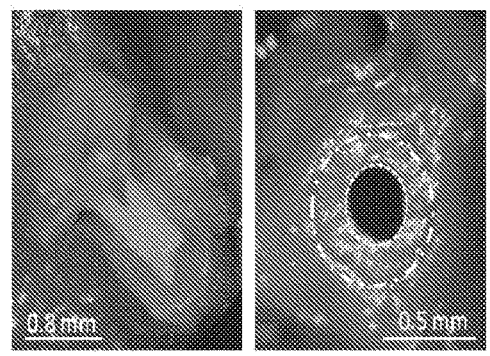
Fig. 1C

TREATMENT FOR AIRWAY CAST OBSTRUCTION

CROSS-REFERENCE TO RELATED APPLICATIONS

This application is a national stage application under 35 U.S.C. 371 of PCT Application No. PCT/US2013/073372 having an international filing date of Dec. 5, 2013, which designated the United States, which PCT application claimed the benefit of priority under 35 U.S.C. 119(e) from U.S. Provisional Application No. 61/733,798 filed Dec. 5, 2012, both of which are incorporated herein by reference in their entirety.

GOVERNMENT SUPPORT

This invention was made with Government support under grant number U54 ES015678 awarded by the National Institutes of Health (NIH). The Government has certain rights in this invention.

FIELD OF THE INVENTION

The field of the present invention is methods for treatment of airway obstruction due to fibrin-containing cast formation.

BACKGROUND OF THE INVENTION

Sulfur mustard (bis(2-chloroethyl)sulfide; SM) is a vesicant and chemical weapon used in warfare during much of the 20$^{th}$ century, and which remains in the stockpiles of multiple nations today (Syria, Iran, North Korea, Libya, United States, and possibly others). SM exposure affects the eyes, skin, upper airways and lungs. After a brief latent period, respiratory failure and death can develop within 12-48 hours. Despite a century of study, the mechanisms responsible for SM's toxic effects remain unsolved, and clinically effective rescue therapies or antidotes are not available.

Initial reports of human SM inhalation toxicity in the early 1900s described the presence of airway obstructive necrotic debris/mucosa, or 'pseudomembranes', in the large airways of victims, and these were more recently confirmed in the victims of the Iran-Iraq war (Eisenmenger, W. et al., 1991, *J Forensic Sci* 36:1688-1698; Willems, J. L., 1989, *Ann Med Milit Belg* 3S:1-61). Severe such lesions have been reported lead to respiratory compromise with need for artificial ventilation, and death in 80% of those needing intubation (Willems, J. L., 1989, *Ann Med Milit Belg* 3S:1-61). Further, chronic conducting airway lesions, such as bronchiolitis obliterans, tracheal/bronchial stenosis and chronic bronchitis, are commonly found in SM inhalation survivors months to years after exposure (Willems, J. L., 1989, *Ann Med Milit Belg* 3S:1-61; Ghanei, M. et al., 2008, *Respir Med* 102:825-830), while chronic alveolar or parenchymal injury is less frequent. Therefore, airway injury predominates during both the acute, as well as the chronic phases of SM-induced lung injury.

Airway obstruction from fibrin casts represents one form of a disorder commonly referred to as plastic bronchitis. This is a rare condition characterized by formation of branching bronchial casts that partially or completely obstruct the tracheobronchial tree, often leading to life-threatening respiratory failure. Even though inhalation of chemicals like sulfur mustard can lead to the development of plastic bronchitis, it can also occur due to causes other than chemical inhalation. While occasionally seen in adults (Watanabe, K. et al., 2008, *Intern Med* 47:1549; Eberlein, M. H. et al., 2008, *Am J Med Sci* 335:163-169), plastic bronchitis not due to chemical inhalation is a disorder affecting mostly children. It can develop after Fontan surgery for congenital cyanotic heart diseases (Goo, H. W. et al., 2008, *Pediatr Radiol* 38:989-993; Do, T. B. et al., 2009, *Pediatr Cardiol* 30:352-355; Costello, J. M. et al., *Pediatrics* 109:e67; Heath, L. et al., 2011, *Pediatr Cardiol* 32:1182-1189; Wakeham, M. K. et al., 2005, *Pediatr Crit Care Med* 6:76-78; Brogan, T. V. et al., 2002, *Pediatr Pulmonol* 34:482-487; Seear, M. et al., 1997, *Am J Respir Crit Care Med* 155:364-370), or after various bronchopulmonary diseases such as asthma (Tonan, M. et al., 2011, *J Anesth; Pawar*, S. S. et al., 2011, *Ann Otol Rhinol Laryngol* 120:697-699), cystic fibrosis (Mateos-Corral, D. et al., 2009, *Pediatr Pulmonol* 44:939-940; Waring, W. W. et al., 1967, *Pediatrics* 39:166-175), acute chest syndrome of sickle cell disease (Moser, C. et al., 2001, *Chest* 120:608-613), viral lower respiratory tract infections including H1N1 (Deng, J. et al., 2010, *Chest* 138:1486-1488), neoplasms such as lymphoma (Kuperman, T. et al., 2006, *Pediatr Pulmonol* 41:893-896), chemical or thermal inhalation injuries (Eberlein, M. H. et al., 2008, *Am J Med Sci* 335:163-169; Pruitt, B. A., Jr., 1974, *Clin Plast Surg* 1:667-691; Cox, R. A. et al., 2003, *Am J Respir Cell Mol Biol* 29:295-302; Veress, L. A. et al., 2010, *Am J Respir Crit Care Med* 182:1352-1361) or idiopathic causes (Krenke, K. et al., 2010, *Respiration* 80:146-147). Presenting symptoms include wheezing, coughing, expectoration of rubbery casts, chest pain, hypoxemia, and/or frank respiratory distress (Brogan, T. V. et al., 2002, *Pediatr Pulmonol* 34:482-487; Madsen, P. et al., 2005, *Paediatr Respir Rev* 6:292-300). Examination of patients with plastic bronchitis, regardless of etiology, reveals wheezing or absent breath sounds over affected regions, while chest radiographs can show segmental lung collapse, or bilateral patchy consolidations often misdiagnosed as pneumonia (Madsen, P. et al., 2005, *Paediatr Respir Rev* 6:292-300). Diagnosis is made either by a history of cast expectoration, or by bronchoscopic or chest CT findings of casts within airways (Eberlein, M. H. et al., 2008, *Am J Med Sci* 335:163-169; Goo, H. W. et al., 2008, *Pediatr Radiol* 38:989-993). Mortality from plastic bronchitis occurs due to respiratory failure related to central airway obstruction, and is more severe in those with underlying cardiac abnormalities (mortality rate of 44-60%) (Brogan, T. V. et al., 2002, *Pediatr Pulmonol* 34:482-487; Madsen, P. et al., 2005, *Paediatr Respir Rev* 6:292-300; Zahorec, M. et al., 2009, *Pediatr Crit Care Med* 10:e34-36).

Treatment of plastic bronchitis, regardless of etiology, has been based primarily on anecdotal evidence reported from individual affected patients. Previously tried medications have included inhaled or systemic corticosteroids (Wang, G. et al., 2006, *Acta Pharmacol Sin* 27:1206-1212), mucolytics (Eberlein, M. H. et al., 2008, *Am J Med Sci* 335:163-169), antibiotics (Shinkai, M. et al., 2005, *Paediatr Respir Rev* 6:227-235), pulmonary vasodilators (Haseyama, K. et al., 2006, *J Thorac Cardiovasc Surg* 132:1232-1233), and anticoagulants such as heparin (Desai, M. H. et al., 1998, *J Burn Care Rehabil* 19:210-212). Non-pharmaceutical treatments have included cast removal via bronchoscopy (Silva, R. C. et al., 2011, *Arch Otolaryngol Head Neck Surg* 137:401-403), vest therapy, fenestration of the Fontan circuit (Wilson, J. et al., 2005, *Pediatr Cardiol* 26:717-719), thoracic duct ligation (Shah, S. S. et al., 2006, *Ann Thorac Surg* 81:2281-2283), AV synchronization (Barber, B. J. et al., 2004, *Pediatr Cardiol* 25:73-76), ECMO (Tonan, M. et al., 2011, *J Anesth*), and heart transplantation for severe cardiac patients (Laubisch, J. E. et al., 2011, *Pediatr Cardiol* 32:1193-1195).

As noted above, SM inhalation is one cause of the rare but life-threatening disorder of plastic bronchitis, characterized by bronchial cast formation, resulting in severe airway obstruction that can lead to respiratory failure and death. Mortality in those requiring intubation is >80%. To date, no antidote exists for sulfur mustard toxicity. Additionally, therapies for plastic bronchitis are solely anecdotal, due to lack of systematic research available to assess drug efficacy in improving mortality and/or morbidity.

SUMMARY OF THE INVENTION

This Summary of the Invention is neither intended nor should it be construed as being representative of the full extent and scope of the present invention. Moreover, references made herein to "the present invention," or aspects thereof, should be understood to mean certain embodiments of the present invention and should not necessarily be construed as limiting all embodiments to a particular description. The present invention is set forth in various levels of detail in the Summary of the Invention as well as in the attached drawings and the Detailed Description and no limitation as to the scope of the present invention is intended by either the inclusion or non-inclusion of elements, components, etc. in this Summary of the Invention. Additional aspects of the present invention will become more readily apparent from the Detailed Description, particularly when taken together with the drawings.

One embodiment of the invention relates to a method to treat airway obstruction in a subject in need thereof, comprising administering to the subject a fibrinolytic agent. In another embodiment, the invention relates to a method to reduce airway obstruction in a subject in need thereof, comprising administering to the subject a fibrinolytic agent. In still another embodiment, the invention relates to a method to increase the survival of a subject having been exposed to a toxic inhaled chemical (TIC), wherein exposure to the TIC results in fibrin-containing cast formation in the airways of the subject, comprising administering to the subject a fibrinolytic agent.

In one aspect, the airway obstructions results from the formation of fibrin-containing casts in the airways of the subject. In another aspect, the subject has been exposed to a TIC. In one aspect, exposure to the TIC results in fibrin-containing cast formation in the airways of the subject. In yet another aspect, the fibring-containing cast formation in the airways of the subject results in the formation of plastic bronchitis in the subject. In still another aspect, the TIC is sulfur mustard or an analog thereof.

The fibrinolytic agent can be selected from tissue plasminogen activator (tPA), a tPA analog, urokinase plasminogen activator (uPA) and a uPA analog. In one aspect, the fibrinolytic agent is tPA. In various aspects, the tPA is administered in a dose amount of about 0.1 mg/kg/dose to about 1.0 mg/kg/dose. In still other aspects, the tPA is administered in a dose amount of about 0.4 mg/kg/dose to about 0.8 mg/kg/dose.

In still another aspect, the fibrinolytic agent is administered to the airways of the subject by a delivery method selected from inhalation, nebulization, aerosolization and intratracheal delivery.

The step of administering can include administering an initial dose of the fibrinolytic agent to the subject followed by administering an additional dose of the fibrinolytic agent to the subject. In one aspect, the step of administering of the fibrinolytic agent is conducted following the exposure of the subject to the TIC. In still another aspect, the step of administering is conducted immediately after an initial exposure of the subject to the TIC. In yet another aspect, the step of administering the fibrinolytic agent is conducted within about 0 hours to about 14 days after an initial exposure of the subject to the TIC. In still further aspects, the step of administering comprises administering an initial dose of the fibrinolytic agent following an initial exposure of the subject to the TIC and administering at least one additional dose of the fibrinolytic agent after the administration of the initial dose of the fibrinolytic agent. In yet another aspect, the step of administering the at least one additional dose is conducted about 30 minutes to about 60 minutes after the administration of the initial dose. In still another aspect, the step of administering the at least one additional dose is repeated. The at least one additional dose can be repeated about every 4 hours to about every 6 hours.

The subject in the invention can be human.

Another embodiment of the invention relates to a kit comprising a fibrinolytic agent selected from tPA, a tPA analog, uPA and a uPA analog and a device for administering the fibrinolytic agent to the airway of a subject.

BRIEF DESCRIPTION OF THE DRAWINGS

FIGS. 1A-1C show a description of cast scoring to assess degree of airways obstruction in plastic bronchitis. (FIG. 1A) Map of the rat lower respiratory tract. During microdissection, extent of airway obstruction was determined at five lobar (main) branches (black lines), and at five major gravity-dependent branches (lines with arrows pointing to them). (FIG. 1B) Nominal cast scoring chart for a given percentage of airway occlusion present. (FIG. 1C) A branching bronchial cast present in the lobar bronchus of the right middle lobe (left panel of FIG. 1C). Also shown is the typical appearance of a cast partially obstructing a central airway visualized en face during microdissection (right panel of FIG. 1C). The dashed white circle (large) denotes normal airway wall perimeter, while the dotted circle (small) denotes the reduced airway lumen size due to cast attachment to the surrounding airway wall. (Image shown in FIG. 1A was obtained from the National Alliance for Medical Image Computing.)

FIG. 8A CEES inhalation but no treatment and followed sequentially for 48 hours; FIG. 8B CEES inhalation and then isoflurane anesthesia twice (5.5 and 6.5 h after CEES) and followed sequentially for 48 hours; FIG. 8C CEES inhalation and then 5 widely separated individual intratracheal tPA (0.7 mg/kg; indicated by vertical dashed lines) doses over 48 hours (each with isoflurane anesthesia); or FIG. 8D CEES inhalation and then 2 narrowly separated individual intratracheal tPA (0.7 mg/kg) doses (at 5.5 and 6.5 h after CEES), with double dosing repeated about 20 h later, and then followed over 48 h. (Rats' SpO$_2$ shown are representative of each treatment group, n=4 per group.) Arrows pointing towards x-axis denote animal's demise at that time point.

analysis at time of euthanasia (at 12 h or earlier if euthanized early due to meeting euthanasia criteria) in rats exposed to SM (3.8 mg/kg) vapor and given no treatment (SM alone, n=5), isoflurane plus intratracheal PBS (SM+PBS, n=8), or isoflurane plus intratracheal tPA (SM+tPA) (0.7 mg/kg, n=8). Significant improvement in bicarbonate level was noted with tPA relative to controls (***p<0.0001, ANOVA for repeated measures, with Tukey's post-hoc analysis) with tPA treatment group resulting in near baseline arterial bicarbonate (<30 mmHg) at time of euthanasia (12 h). Values represent mean bicarbonate with error bars for SEM.

Figure 14:
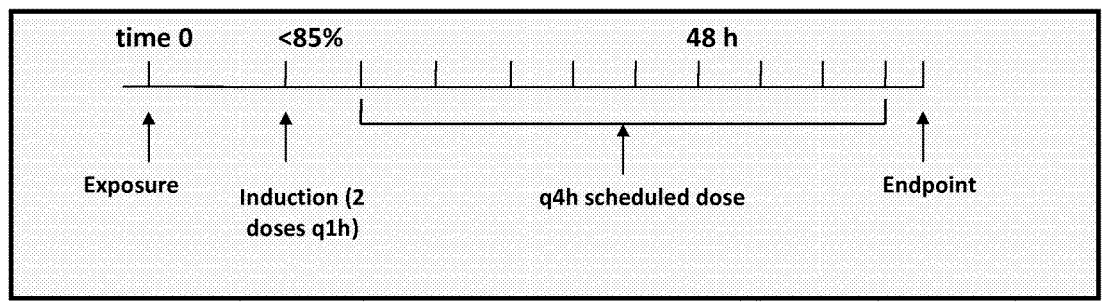

FIG. 14 shows an overall procedural design for administering tPA over 48 hours following exposure to SM. Rats were exposed and then monitored by pulse oximetry (pOx) and clinical examination hourly until randomization (oxygen saturation <85%, or >10% drop from baseline of ~97% at sea level) to either of 3 groups: 1) SM+no treatment (NT, or SM alone, n=12), 2) SM+placebo (PBS, n=13; q4 h), or 3) SM+tPA treatment (n=9; q4 h). Animals were then monitored every 2 hours after induction treatment dose, and were given a maintenance tPA (or PBS) treatment dose every 4 hours (q4 h). All rats given intratracheal tPA or PBS received this by direct intratracheal instillation via an atomizer placed through the vocal cords into the mid-trachea by direct laryngoscopy under isoflurane anesthesia. Rats were monitored continuously for 48 hours for distress, euthanasia criteria assessment, and periodic (q2 h-every 2 hours) pulse oximetry/clinical distress scoring assessments. tPA dosing: 0.7 mg/kg (induction is 2 doses 1 hour apart), then 4qh maintenance dose (1 dose). The euthanasia critea (must meet both): pOa<70% and clinical score > or =7. Endpoints: survival; pOx q1-2 hours and at euthanasia; clinical scoring q1-2 and at euthanasia; arterial blood gas (ABG) at euthanasia (pO2, pCO$_2$, pH, Bicarb); electrolytes and hematocrit (Hct) at euthanasia (glucose, sodium, calcium, potassium, lactate, Hct); airway obstruction score. See FIGS. 15-26 below.

Figure 15:
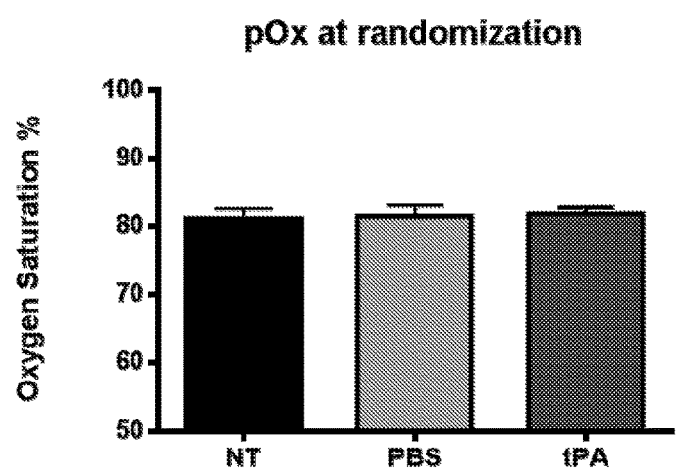

FIG. 15 shows the pulse oximetry values (estimated arterial oxygen saturation; percent saturation) in each group from FIG. 14 at the time of randomization. None were statistically different from the other (mean of ~81%). All groups received SM.

Figure 16:
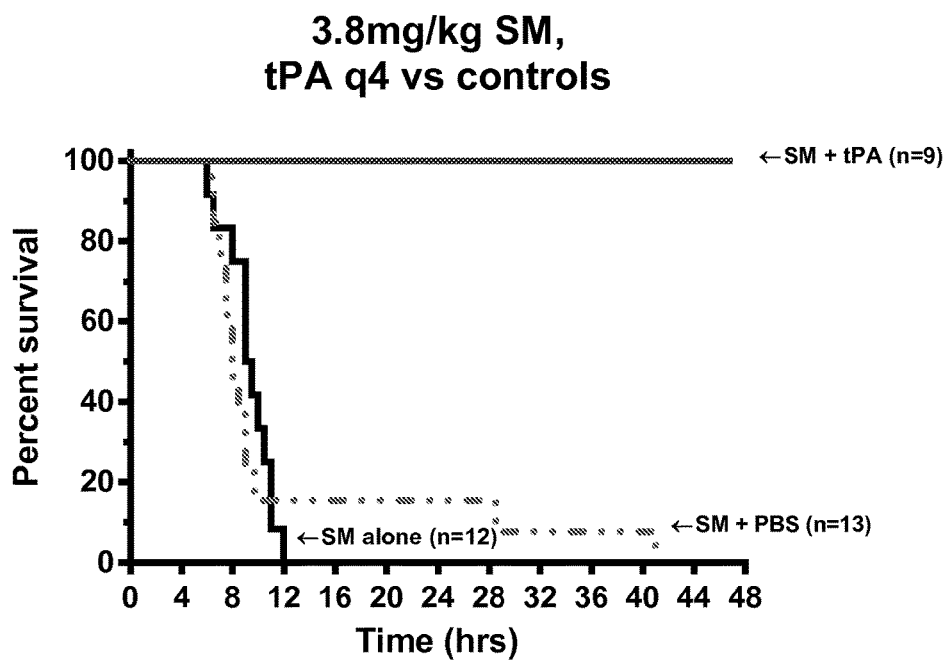

FIG. 16 shows the percent survival of rats in each group from FIG. 14 over the 48 hour study period. Survival curves for rats exposed to SM (3.8 mg/kg) and given: 1) SM alone (n=12), 2) SM+PBS (placebo, n=13), or 3) SM+tPA treatment (n=9). Both control groups had 0% survival at 48 h, while tPA treatment had 100% survival (p<0.0001, Log-rank, Mantel-Cox test). tPA treatment completely eliminated mortality (48 h) after sulfur mustard (SM) inhalation, with no deaths within 48 h period, in contrast to 100% mortality in both SM alone and PBS treated control groups (median time to death was 8 h in SM alone group, and 9 h in PBS-treated group). Rats were electively euthanized when in severe distress, as directed by the Institutional Animal Care and Use Committee (IACUC) protocol, when they had sustained oxygen saturations below 70% in association with a clinical score of 7 or greater (9 being maximally severe, as indicated by severity of respiratory distress and inactivity).

Figure 17:
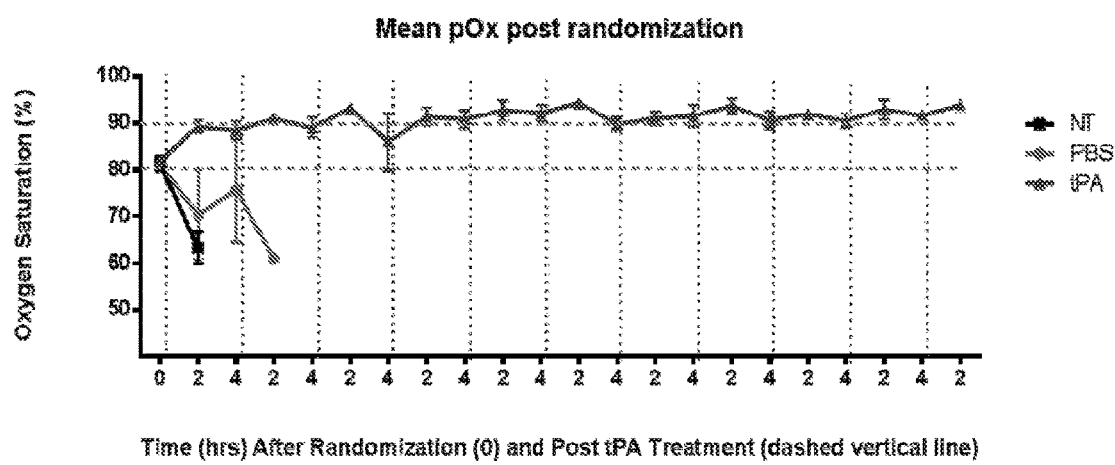

FIG. 17 shows the mean±SEM pulse oximetry values for rats tracked in the three treatment groups (from FIG. 14) from the time of randomization. Those given no treatment (SM alone, NT) all died within 2 hour of randomization, while placebo treated animals (PBS) died within a few hours thereafter. In contrast, tPA treated animals (tPA-top line) given PBS after their initial dosing, showed a more gradual decline in pulse oximetry results. tPA treatment resulted in saturation improvement from nadir of <84% to near 90% after the first induction dose, with continued overall saturations >90-92% for the remainder of the study (to 48 h).

Figure 18:
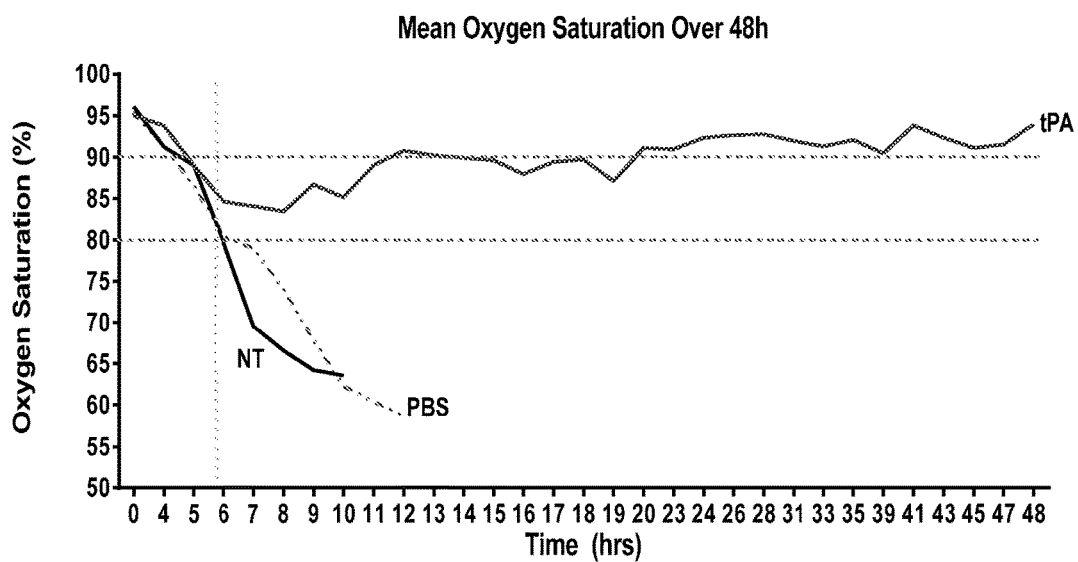

FIG. 18 shows the pulse oximetry results from exposure (time 0) for 48 hours in tPA versus controls after SM exposure. Note that this figure shows data from the time of exposure, and not from randomization, thereby each animal receiving therapies at different times on this graph. tPA treatment resulted in saturation improvement from nadir of <84% to above 90% by 12 h after exposure, with continued overall saturations >90-92% for the remainder of the study. Controls had severe oxygen saturation deterioration within hours of exposure, resulting in eventual death. (Vertical dotted line=median time of first induction dosing).

Figure 19:
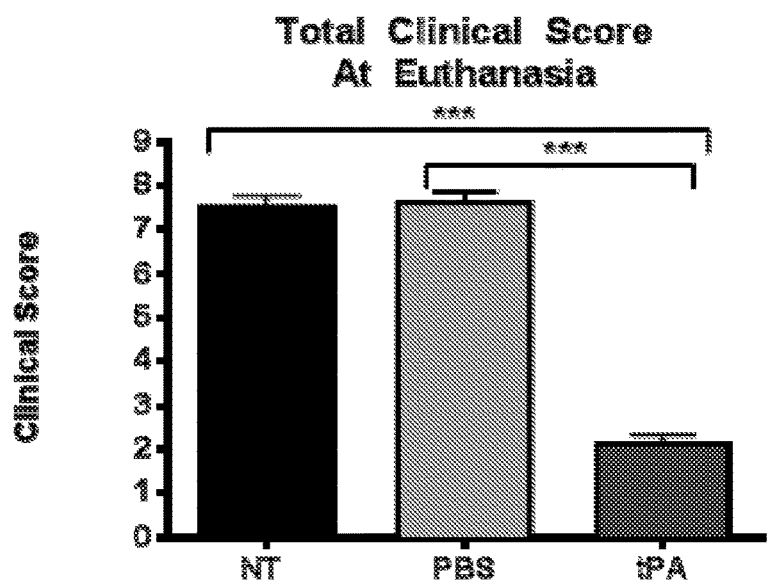

FIG. 19 shows the clinical scores at euthanasia (elective or at 48 hour termination) in all groups from FIG. 14. Clinical distress was greatly improved after tPA treatment. Distress was monitored in rats after SM exposure (3.8 mg/kg) hourly for 48 hours. Combined clinical distress score encompassed respiratory distress (0-6) as well as activity (0-3), with a total score of 9 indicating maximal distress. SM exposure alone (NT), as well as placebo treatment (PBS) resulted in severe distress, while tPA treatment (tPA) minimized animal distress despite high dose SM inhalation. *** denotes p<0.0001

Figure 20:
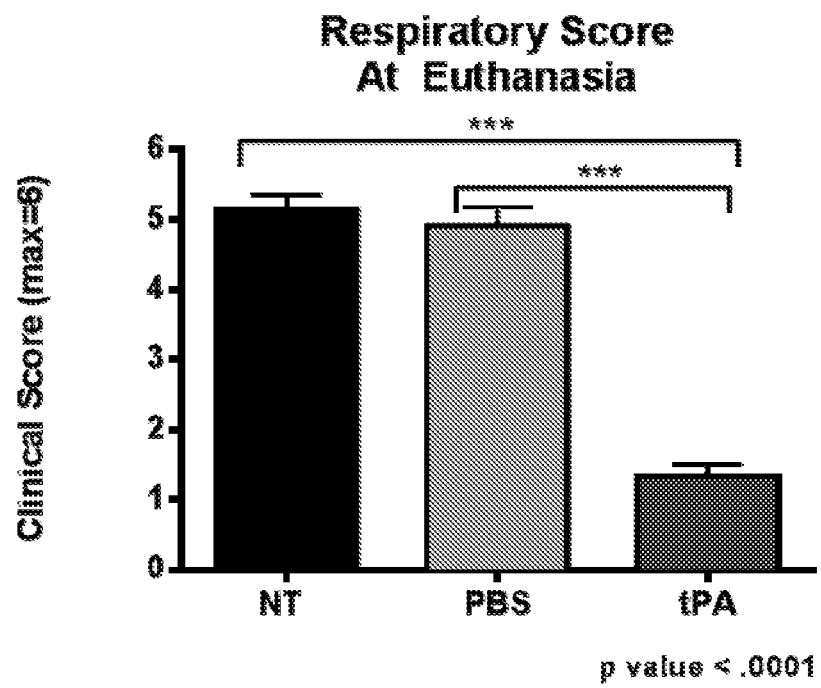

FIG. 20 shows the respiratory quality scores at euthanasia in all groups from FIG. 14. The maximum (worst) score here is 6. Respiratory distress was greatly improved after tPA treatment (tPA), while controls (no treatment (NT) and placebo (PBS) had severe distress. *** denotes p<0.0001

Figure 21:
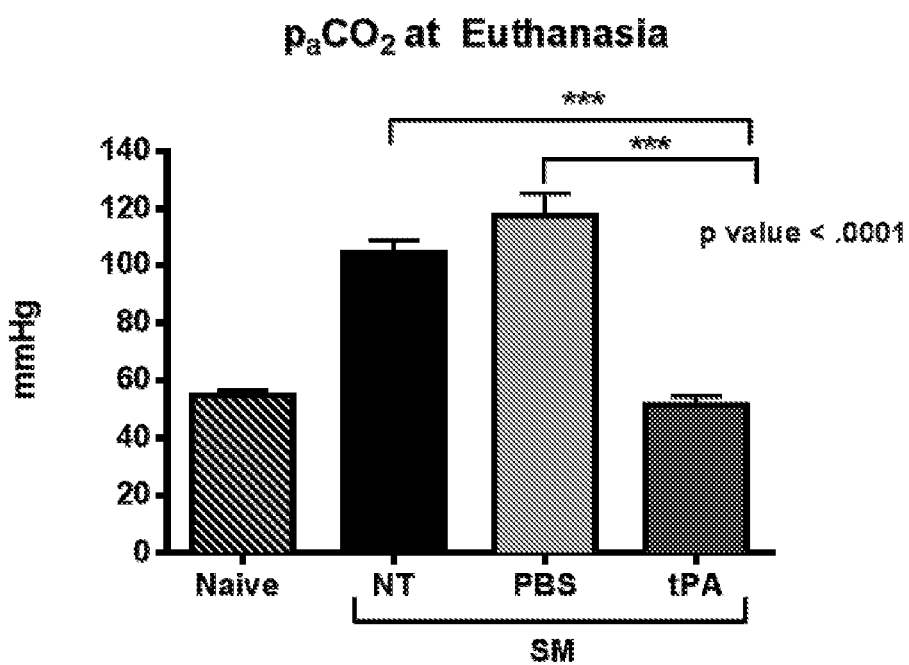

FIG. 21 shows the arterial pH in naïve animals (air breathing) and all groups (from FIG. 14) at euthanasia. Profound acidosis in the SM-exposed (no treatment, NT) and placebo-treated animals (PBS) was detected, and the normal pH (naïve) was detected at euthanasia in tPA-treated animals (tPA). ***p<0.0001

Figure 22:
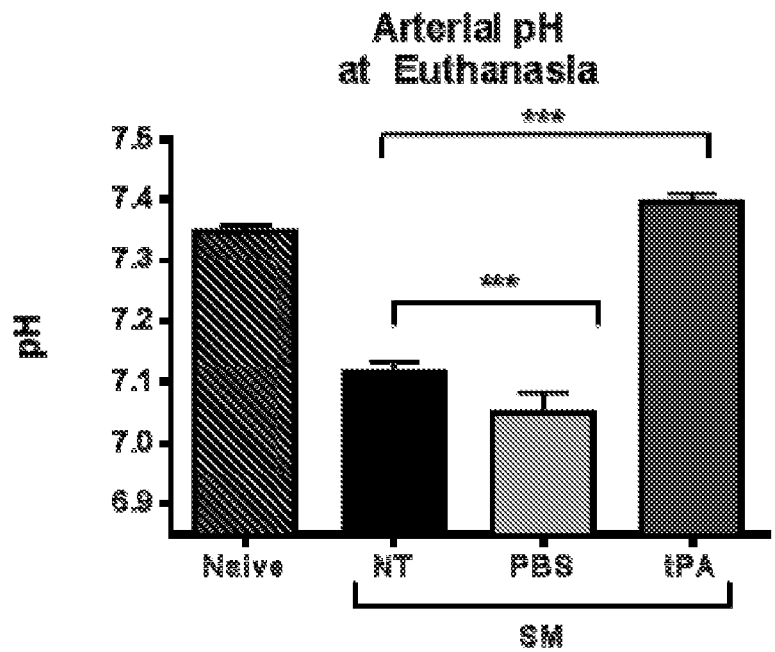

FIG. 22 shows the arterial carbon dioxide tension (p$_a$CO$_2$, mm Hg) in naïve animals and all groups from FIG. 14 at euthanasia. These were obtained invasively under anesthesia by aortic puncture. Marked hypercarbia in the SM-exposed (non-treated, NT) and placebo-treated animals (PBS) was detected, consistent with a severe ventilation defect. tPA treatment (tPA) resulted in normal arterial CO$_2$ levels, corresponding to a normal ventilation response despite SM exposure. ***p<0.0001

Figure 23:
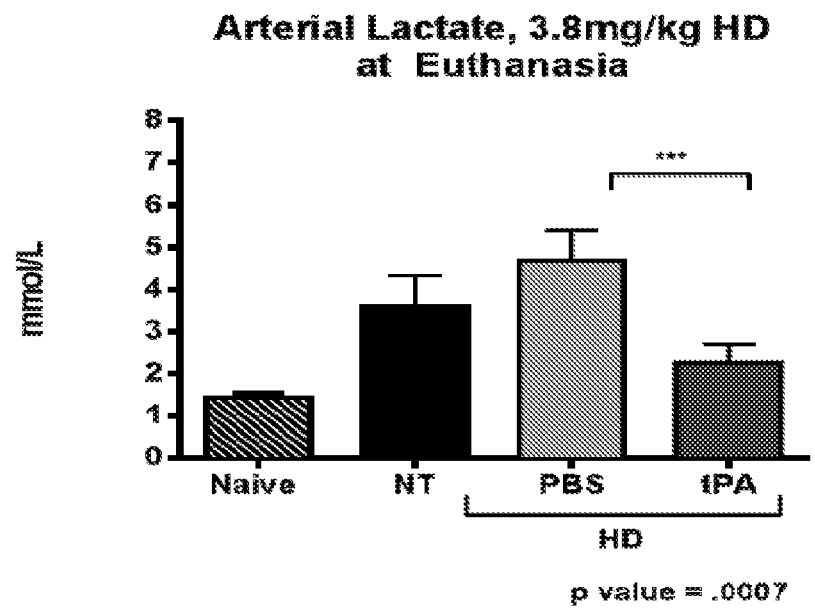

FIG. 23 shows the blood lactate (mmol/L) in naïve animals and all groups from FIG. 14 at euthanasia. SM is referred to as "HD" in this figure. Note the tendency for elevated lactate in all groups. Elevation of blood lactate indicates suboptimal tissue oxygen delivery and suggests that the sick animals had both respiratory and metabolic acidosis. Notably, only rats in the tPA treatment group had lactate values comparable to air-breathing naïve controls.

Figure 24:
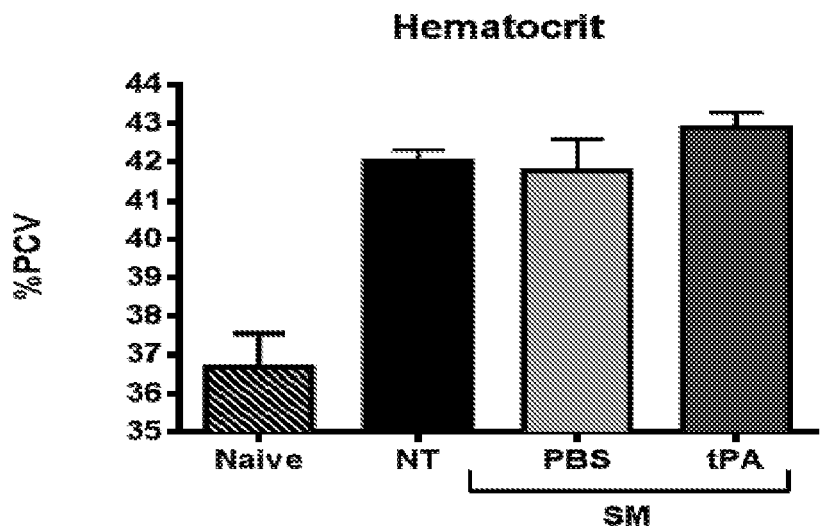

FIG. 24 shows the hematocrit values (percent packed cell volume (PCV)) for naïve animals and the three SM-exposed groups from FIG. 14. Hematocrits were not decreased in tPA-treated groups, suggesting that there was no blood loss in these animals.

Figure 25:
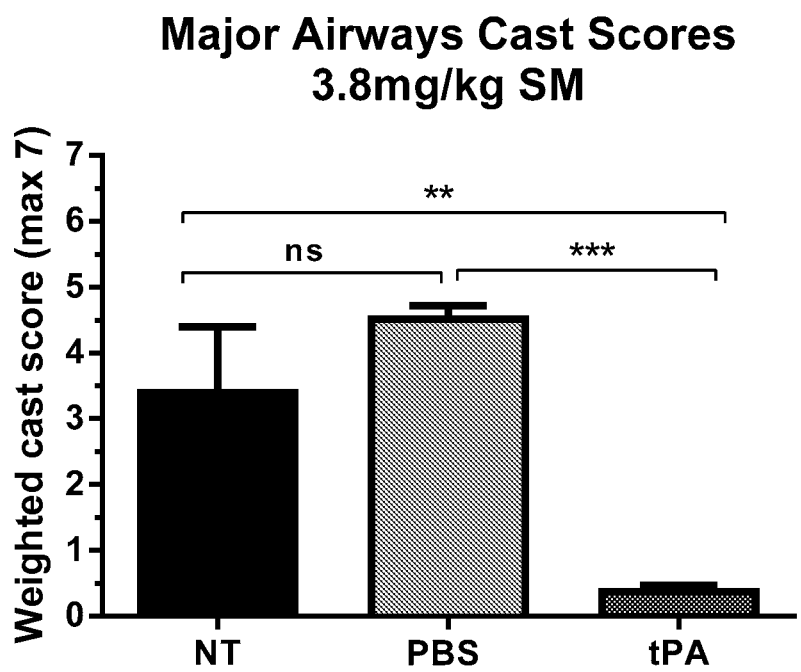

FIG. 25 shows airway obstruction scores by fibrin casts in the three groups from FIG. 14 after SM exposure. Casts were revealed by airway microdissection after lung fixation (at euthanasia or 48 h) of all major central lobar bronchi (5 lobes). These scores are obtained after microdissection of the trachea and all five lobes by morphometric study to quantitate the percent airway occlusion of each of the five main lobar bronchi by fibrin casts. These methods are described in Veress, L. A., et al. *American Journal of*

*Respiratory Cell and Molecular Biology* 2013 48:4, 439-447. A score of 7 indicates 100% occlusion of all 5 main bronchi. Briefly, the percent airway occlusion by cast was measured, then converted to a nominal score, weighted per ratio of lobar volume to total lung, then added for a composite score. HD-exposed and PBS-treated rats had scores exceeding 50% airway occlusion overall, while airway occlusion of main lobar bronchi in tPA-treated rats was negligible (score 4=50-65% total airway luminal occlusion). $p<0.0005$, ANOVA, Tukey's post-hoc analysis ( denotes $p<0.001$, and * denotes $p<0.0001$).

Figure 26:
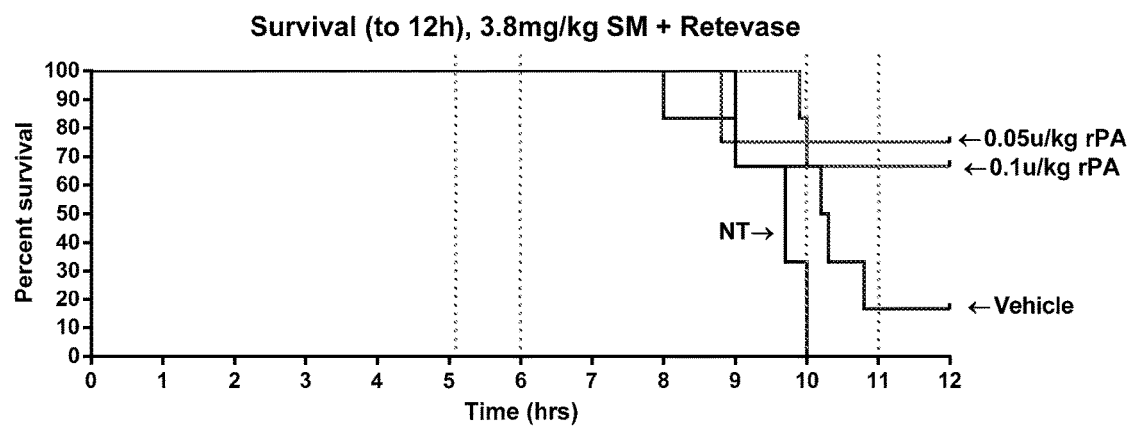

FIG. 26 shows the results of retevase (rPA) treatment as compared to various controls following exposure to SM inhalation. The effect on survival is shown. Rats given no treatment (NT) had all succumbed by 10 hours. Vehicle used was the diluent for rPA, containing small amounts of polysorbate 80, sucrose, phosphoric acid, dipotassium hydrogen phosphate and tranaxemic acid in quantities provided by rPA supplier. Rats treated with vehicle only had 80% mortality (or 20% survival) by 12 hours. By contrast, rats treated with rPA 0.05 unit/kg per dose, or with rPA 0.10 unit/kg per dose showed >65% survival by 12 hours. rPA treatment occurred at 5 and 6 hrs, for induction, and a second treatment at 10 and 11 hrs, via intratracheal instillation as performed with tPA previously. The highest survival rate (75%) was in the group of rats given the lower dose of rPA (0.05 unit/kg/dose).

Figure 27:
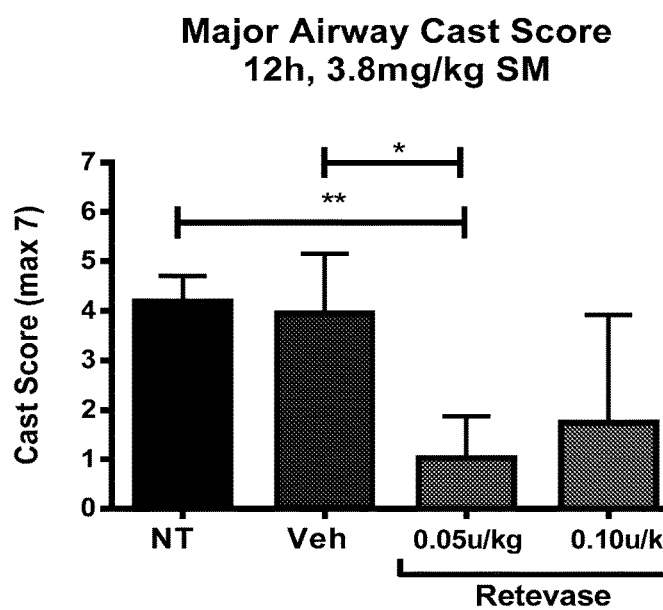
Figure 28:
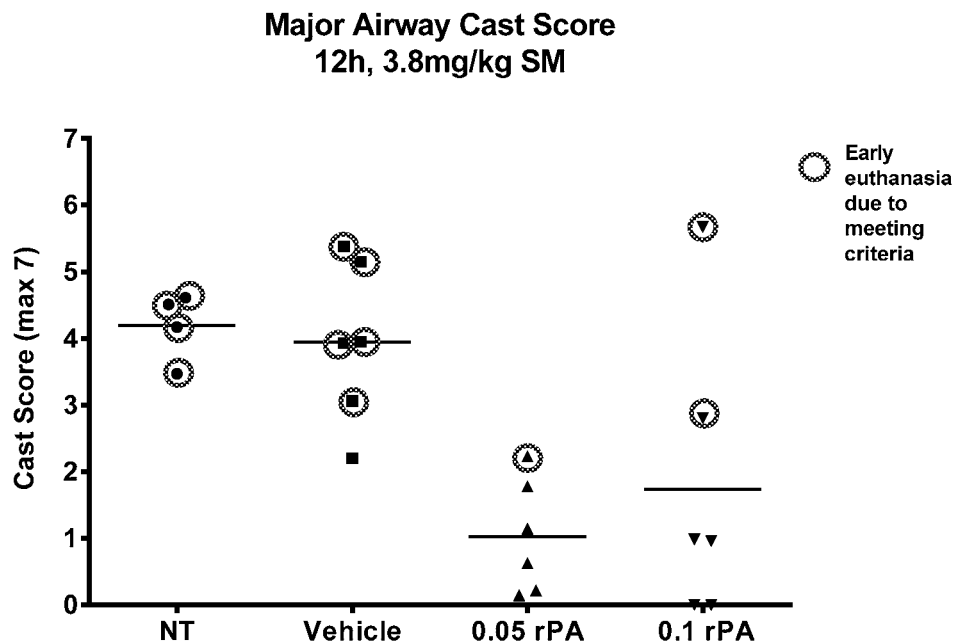

FIG. 27 shows the effect of rPA on major airway cast scores at 12 hours after SM exposure. Cast scores for no treatment (NT, n=4) and drug diluent (vehicle, Veh, n=6) were both approximately 4, indicating that >50% of the total airway internal luminal areas were occluded. By contrast, mean major airway cast scores for both rPA dose groups (0.05 u/kg, n=5, and 0.1 u/kg, n=6) were each less than half of this level, and with the result for cast score for the lower dose of rPA being statistically significantly different from both control groups. * denotes $p<0.05$, and ** denotes $p<0.001$ FIG. 28 illustrates the individual data disclosed in FIG. 15, with circled data points indicating those animals that required early euthanasia (prior to 12 hour study termination).

Figure 29:
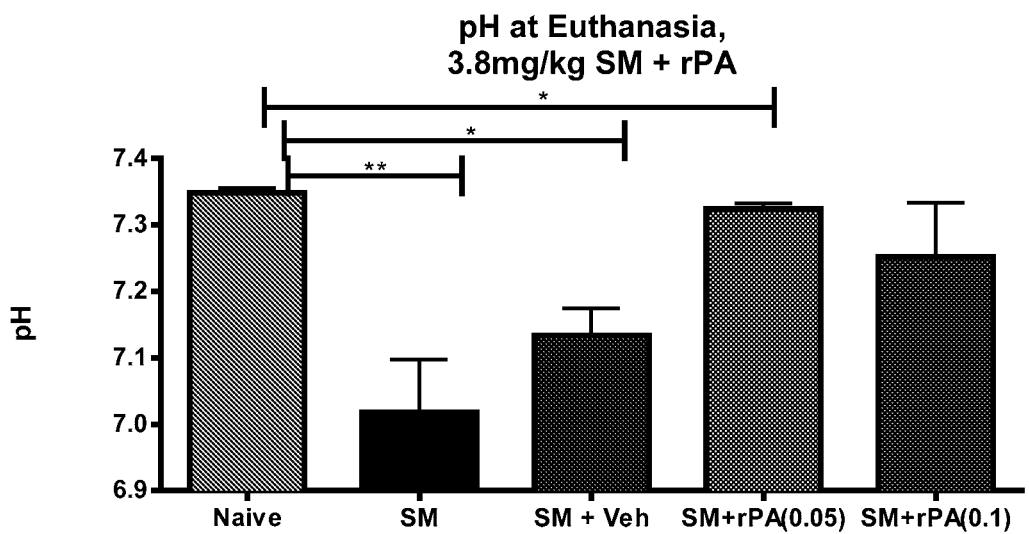
Figure 30:
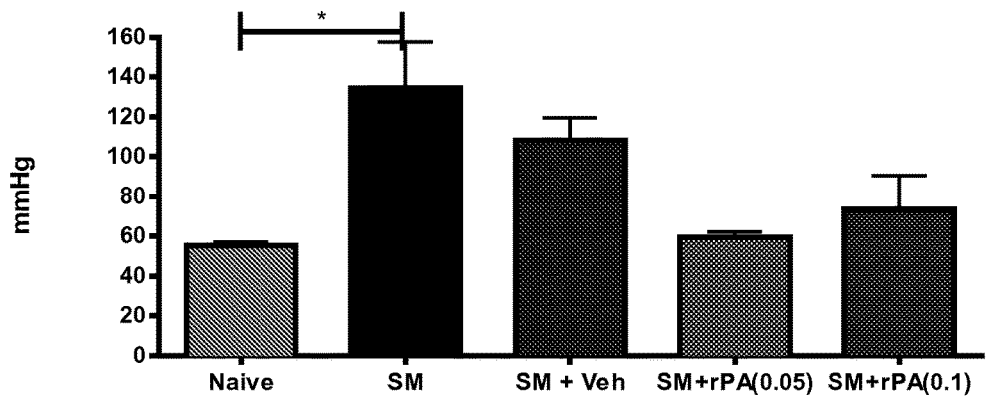
Figure 31:
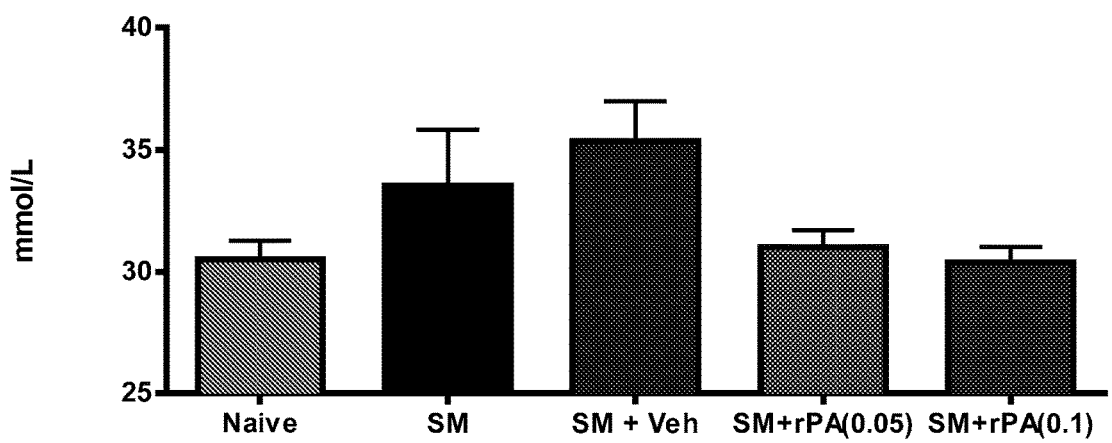

FIG. 29 shows the arterial blood pH values for rPA treated rats versus those of various control groups after SM exposure. Rats treated with the lower dose of rPA had arterial pH values that were significantly different from those of rats treated with vehicle (SM+Veh) or exposed to SM alone. The values for rats treated with the lower dose of rPA had arterial pH values comparable to those of naïve rats not exposed to sulfur mustard (i.e. >7.30). * denotes $p<0.05$, and ** denotes $p<0.001$ FIG. 30 shows the arterial blood carbon dioxide content of rats treated with rPA (0.05 unit/kg per dose; 0.10 unit/kg per dose) versus those of 3 control groups (naïve, with vehicle (SM+Veh) or exposed to SM alone). All rats in these studies, as in FIG. 29, were anesthetized prior to their blood being drawn. Carbon dioxide levels were near naïve levels at 12 h with rPA treatment. * denotes $p<0.05$ FIG. 31 shows that rats exposed to SM and treated with either dose of rPA (0.05 unit/kg per dose or 0.10 unit/kg per dose) had plasma bicarbonate (e.g. carbon dioxide contents in mmol/L) that were low and comparable to those of naïve rats. Meanwhile, elevated bicarbonate levels were noted in the SM alone and the SM+Vehicle treated groups.

Figure 32:
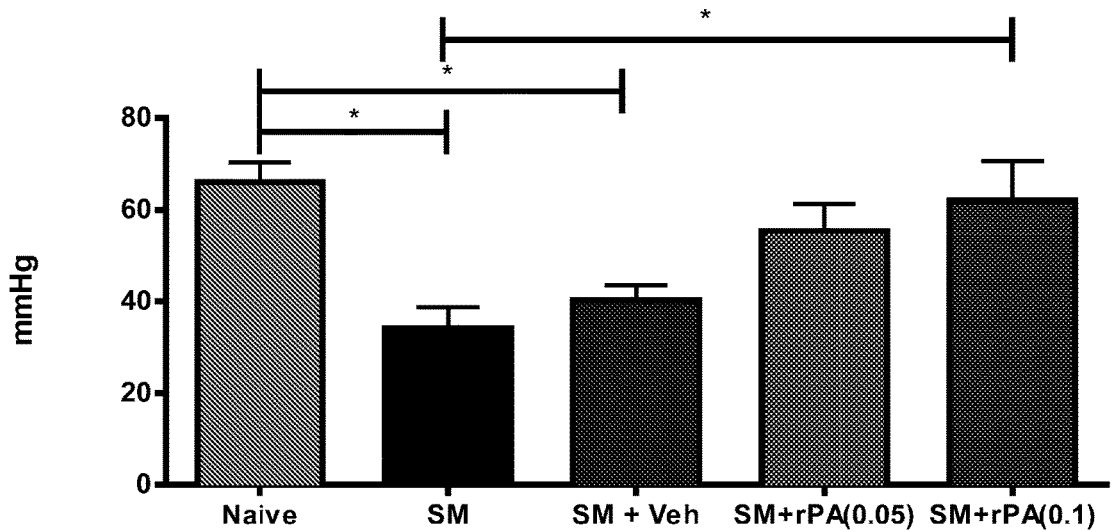
Figure 33:
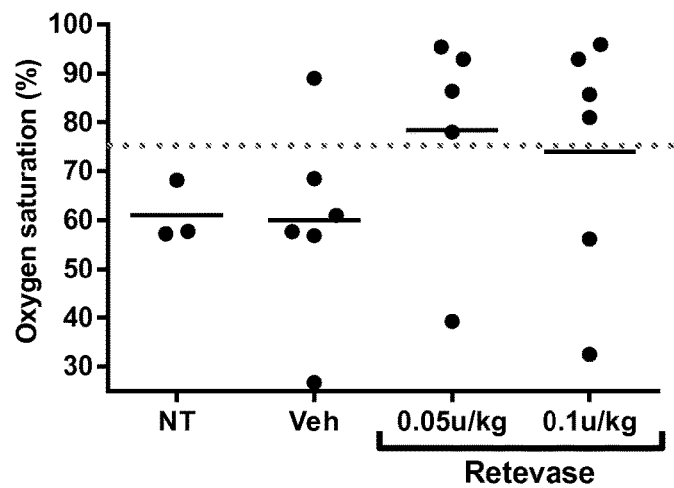

FIG. 32 shows the arterial blood oxygen content (partial pressure of oxygen; $p_aO_2$) of anesthetized animals at euthanasia (12 h or earlier of met criteria for euthanasia) after exposure to SM and treated with rPA. SM exposure caused a marked decline in this value compared to those of naïve animals. SM+Veh rats had comparable values for $p_aO_2$ as those seen in SM alone-exposed rats. By contrast, rats exposed to either dose of rPA (0.05 unit/kg per dose or 0.10 unit/kg per dose) after SM exposure had statistically improved values for $p_aO_2$ as compared to those for rats given SM or SM+Veh, and these values for rPA-treated rats were comparable to those seen in naïve rats. * denotes $p<0.05$ FIG. 33 shows the individual rat pulse oximetry values at euthanasia (12 h or earlier if euthanasia criteria was met), in rats exposed to SM and given no treatment (NT), vehicle for rPA (Veh), or either of two doses of rPA (0.05 units/kg per dose or 0.10 units/kg per dose). The dotted horizontal line denotes all animals who were alive at 12 h study completion (above dotted line), or euthanized prior to 12 h due to severe distress (below dotted line).

DETAILED DESCRIPTION

This invention generally relates to methods for treating airway obstruction in a subject and/or to reduce airway obstruction in a subject as well as for increasing the survival of a subject having airway obstruction. The invention includes the administration of a fibrinolytic agent.

The airway obstruction may result from the formation of fibrin-containing casts in the airways, which can include airspaces, of the subject, including but not limited to the trachea, bronchi and more distal airways.

The formation of the fibrin-containing casts may be the result of the subject having been exposed to a toxic inhaled chemical (TIC). In one aspect, the exposure to the TIC results in fibrin-containing cast formation in the airways and/or airspaces of the subject. In still another aspect, the fibrin-containing cast formation in the airways and/or airspaces of the subject results in the formation of plastic bronchitis.

The toxic inhaled chemical, can be sulfur mustard (SM) also referred to herein as HD ("Hun Stuff Distilled") or authentic sulfur mustard, sulfur mustard analogs (such as CEES), Bhopal agent and other agents that are known to cause fibrin casts. The TIC can be formulated into a vapor form as well as into an aerosol form, a gas form, particulate forms and combination thereof. In a preferred embodiment, the TIC is formulated into a vapor form. In one aspect, the aerosol form of the TIC could be formulated into an ethanolic solution.

The fibrinolytic agent may be any fibrinolytic compound. The fibrinolytic compound can be a plasminogen activator. In one aspect, the plasminogen activator can be a tissue plasminogen activator (tPA) such as tenectaplase (TNK) or a recombinant tPA (such as rh-TPA), a tPA analog, a urokinase plasminogen activator (uPA), a uPa analog and combinations thereof. An analog of tPA or uPA can include a portion of the tPA or uPA, such as a single chain uPa or tPA. In a preferred embodiment, the fibrinolytic agent is tPA.

Over the past three decades, tPA has become accepted therapy for a spectrum of intravascular events, including acute myocardial infarction (1993, *N Engl J Med* 329:1615-1622), thrombotic stroke (Lansberg, M. G. et al., 2012, *Chest* 141:e601S-636S), acute pulmonary embolism and severe deep vein thromboses (Kearon, C. et al., 2012, *Chest* 141:e419S-494S). It also can be useful in removing clots from blocked catheters and grafts (arteriovenous shunts) (Hilleman, D. et al., 2011, *Pharmacotherapy* 31:1031-1040), treatment of unusual acute thrombotic events (Garcia, A. et al., 2011, *J Pediatr Surg* 46:2021-2024), treatment of empyemas and pleural effusions (Rahman, N. M. et al., 2011, *N Engl J Med* 365:518-526), and to limit amputation in frostbite (Johnson, A. R. et al., 2011, *Foot Ankle Spec* 4:344-348). tPA also can be useful in animal models for treating a variety of extravascular fibrin deposition disorders including prevention of intra-abdominal adhesions 9 van Goor, H. et al., 1996, *Eur Surg Res* 28:287-294), and clearance of airways after burns and smoke inhalation (Enkhbaatar, P. et al., 2004, *Shock* 22:70-75). In addition, it has been reported anecdotally as beneficial therapy for patients with plastic bronchitis after Fontan procedure in congenital heart disease (Do, T. et al., 2009, *Pediatr Cardiol* 30:352-355; Costello, J. M. et al., 2002, *Pediatrics* 109:e67; Wakeham, M. K. et al., 2005, *Pediatr Crit Care Med* 6:76-78).

tPA is also currently used as first-line therapy in several clot-associated diseases such as stroke (Barreto, A. D. et al., 2012, *Stroke* 43:770-775; Kablau, M. et al., 2012, *Int J Stroke*) and myocardial infarction (Fitchett, D. H. et al., 2011, *Can J Cardiol* 27 Suppl A:S402-412), and can improve survival with these life-threatening entities. In regards to plastic bronchitis, no placebo-controlled clinical trials have been done to evaluate the effects of tPA. For this reason, it is unknown if tPA can truly alter mortality and/or morbidity measures associated with plastic bronchitis. Furthermore, the proper dose required for tPA efficacy has not yet been assessed in vivo.

The fibrinolytic agent may be administered to the subject by any airway or intra-airway delivery method. Such methods are known in the art and include but are not limited to administration by inhalation, nebulization, aerolization and/or intratracheal delivery. Nebulized tPA, nor any other form of airway-delivered tPA or fibrinolytic agent, is not believed to have been known to have been used for treatment of any TIC. Another possible mode of administration is to intubate a subject (for example a subject on a ventilator) and attach a nebulizer to the endotracheal tube (ETT) for delivery of the fibrinolytic agent. Other modes of administration can be via direct administration into the airways, such as by bronchoscopy or intubation or bronchoscopy thru a newly placed ETT. In a preferred embodiment the fibrinolytic agent is administered to the subject by intratracheal delivery.

In another embodiment, the subject is administered a dose of the fibrinolytic agent. The subject may be administered an initial dose (i.e. loading dose) followed by a second or additional dose at a later time point at the onset of therapy (referred to as loading regimen). In still a further embodiment, the subject may be administered an initial dose followed by at least one additional dose of the fibrinolytic agent.

In one embodiment, the initial dose is administered following exposure of the subject to a TIC. In another embodiment, the initial dose is administered immediately after an initial exposure of the subject to the TIC. In still another embodiment, the initial dose can be administered within about 1 hour, about 2 hours, about 3 hours, about 4, about 5 hours, about 6 hours, about 7 hours, about 8 hours, about 9 hours, about 10 hours, about 12 hours, about 14 hour, about 16 hours, about 20 hours, about 24 hours, about 48 hours, about 72 hours, about 4 days, about 8 days, about 12 days about, about 14 days or times in between, after an initial exposure of the subject to a TIC.

The additional dose or at least one additional dose can be administered at least 30 minutes after the administration of the initial dose, at least one hour after the administration of the initial dose, at least two hours after the administration of the initial dose, at least 5 hours after the administration of the initial dose, at least 24 hours after the initial dose, at least 48 hours after administration of the initial dose or any time in between. Preferably, the additional or second dose is administered about 30 minutes to one hour after administration of the initial dose.

The dosing regimen of administering an initial dose followed by at least one additional dose at a later time point at the onset of therapy (i.e. the loading regimen), may be repeated as often as necessary. The loading regimen can be repeated about every 3 hours, about every 4 hours, about every 8 hours, about every 16 hours, about every 20 hours, about every 24 hours, about every 36 hours, about every 72 hours, about every 5 days, about every 10 days, about every 20 days, about every 30 days, about every 45 days, about every 6 months or about every year. Preferably, the repeated dosing regimen is repeated about every four hours to about every six hours.

To determine if re-dosing is needed following the initial loading regimen, oxygen saturation levels may be determined in the subject. If the oxygen saturation levels in the subject drop below an unacceptable level, such as 85-90%, the re-dosing loading regimen may be initiated again (one dose followed by a second dose at a later time point). It is possible that the subject may only need to be administered a single additional dose instead of the loading regimen. The re-dosing can occur about every 3 hours, about every 4 hours, about every 8 hours, about every 16 hours, about every 20 hours, about every 24 hours, about every 36 hours, about every 72 hours, or about every 5 days, about every 10 days, about every 20 days, about every 30 days, about every 45 days, about every 6 months or about every year or until no more oxygenation changes occur. The repeated dosing may be dependent upon the oxygenation decline due to plastic bronchitis, which induces cast formation. Repeated dosing can be done on a scheduled basis or can be done on an as needed basis (i.e. 'pro re nata' (PRN) basis).

The dose amount may be in a range having a lower endpoint from about 0.10 mg/kg/dose, about 0.15 mg/kg/dose, about 0.20 mg/kg/dose, about 0.25 mg/kg/dose, about 0.30 mg/kg/dose, about 0.35 mg/kg/dose, about 0.40 mg/kg/dose, about 0.45 mg/kg/dose or about 0.50 mg/kg/dose. In addition, the effective dose may be in a range having an upper endpoint of about 1.0 mg/kg/dose, about 0.95 mg/kg/dose, about 0.90 mg/kg/dose, about 0.85 mg/kg/dose, about 0.80 mg/kg/dose, about 0.75 mg/kg/dose, about 0.70 mg/kg/dose, about 0.65 mg/kg/dose, about 0.60 mg/kg/dose or about 0.55 mg/kg/dose. In a preferred embodiment, the dose is about 0.70 mg/kg/dose. For tPA, the dose amount can be about 0.1 mg/kg/dose to about 1.0 mg/kg/dose with a preferred amount of about 0.4 mg/kg/dose to about 0.8 mg/kg/dose. The dose amount can be weight adjusted for the subject. The dose amount can be adjusted based on the administration route. A direct administration routes, such as by bronchoscopy or intubation, the tPA dose amount may range in an amount of about 0.1 mg/kg/dose to about 1.0 mg·kg/dose. The dose amount that can be administered can also be the equivalent milligram amount of the fibrinolytic agent required to deliver an equivalent plasminogen activator activity as compared to a 0.1 mg/kg/dose to a 1.0 mg/kg/dose of tPA, specifically rh-tPA (Genetech). Plasminogen activator activity can be used to detect the activities of tPA, uPA and analogs thereof in vitro. Such activity can be determined using known plasminogen activator activity assays, including fluorescent-based assays. The assays can use native fibrin in the bottom of a multi-well plate, or they can be used in solution working with fluorescent substrates for plasmin that serve as a surrogate for fibrin. One such substrate is D-ala-leu-lys-7-amido-4-methylcoumarin. The 'activity' can be detected as long as the incubation contains this substrate (D-ala-leu-lys-7-amido-4-methylcoumarin) and a plasminogen (such as rat plasminogen or human plasminogen). The assay is relatively linear over a broad range of tPA or uPA activities. The activity can be inhibited by a relatively specific inhibitor such as PAI-1 (plasminogen activator inhibitor-1) or a nonspecific protease inhibitor such as leupeptin.

In still another embodiment, the subject is a mammal, including but not limited to a human, dog, and cat. In yet another embodiment, the subject is a human child.

In still another embodiment, the fibrinolytic agent may be provided in a kit and/or a container. The kit can include a fibrinolytic agent such as those disclosed herein, including tPA, a tPA analog, uPA and a uPA analog as well as including a device for administering the fibrinolytic agent to the airways, including the airspaces of the subject. The device for administering the fibrinolytic agent to the airways are well known in the art and can include an atomizer, a nebulizer, a catheter, a bronchoscope, endotracheal tube, tracheostomy tube or a laryngeal mask airway, or any combination of these modes.

In yet another embodiment, the fibrinolytic agent and a pharmaceutically acceptable carrier may be administered to the subject. Such carriers are well known to those in the art.

In still yet another embodiment, the fibrinolytic agent may be administered to subject followed by administration of an anticoagulant such as heparin or Tissue Factor Pathway Inhibitor (TFPI) at a time point following the administration of the fibrinolytic agent.

As disclosed in the Example section below, the Inventors have found that optimal intratracheal tPA treatment for SM and an SM analog (CEES) induced severe plastic bronchitis in rats eliminated mortality in this almost uniformly fatal disease model, and that tPA also greatly improved other morbidity outcome measures often associated with plastic bronchitis. The Inventors found that a tPA dose of 0.7 mg/kg/dose delivered intratracheally, via a two-dose regimen given 1 hour apart, followed by repeated treatments during the 48 hour interval, resulted in 0% mortality by 48 hours after plastic bronchitis induction with SM and an SM-analog inhalation, compared to 90% mortality with no treatment, and 100% mortality in both PBS and isoflurane controls. Furthermore, improved morbidity with tPA was evidenced by normalization of plastic bronchitis-associated hypoxemia, hypercarbia, and acidosis, as well as by dose-dependent improvements in both respiratory distress and airway fibrin casts (i.e. Main and Dependent Bronchi composite cast scores) after treatment. Using a systematic approach, the Inventors have demonstrated the first in vivo dosimetric assessment of intratracheal tPA efficacy on survival and morbidity in plastic bronchitis, induced by inhalation of a sulfur mustard analog inhalation as well as following inhalation of authentic SM (referred to herein as "SM").

Previously, it has been reported that plastic bronchitis can result from acute inhalation of toxic chemicals such as a sulfur mustard analog (for example CEES), via a mechanism involving damage to the bronchial circulation, with resultant leakage of plasma contents into airways (Veress, L. A. et al., 2010, *Am J Respir Crit Care Med* 182:1352-1361). The Inventors have shown that fibrin-containing casts occluded conducting airway generations 3-15, the region of bronchial artery distribution, and that indeed, the entire bronchial circulation had greatly increased permeability. Disclosed herein, it is shown that the resulting airway obstruction from casts leads to impaired gas exchange and tissue oxygenation, respiratory distress, and often death. In addition, even when treatment is delayed for several hours after injury the Inventors demonstrate that tPA can reverse airway fibrin deposition, resulting in improved gas exchange and tissue oxygenation, eliminating respiratory distress and death as demonstrated in a relevant animal model of toxic chemical inhalation disclosed herein. This is a considerable advance relative to previously reported findings, as it supports that, not only do airway obstructive lesions stain positively by fibrin, but, further, that the airway obstructive lesions are responsible for the gas exchange abnormalities, clinical respiratory distress and mortality in this model. Thus, fibrin is not just immunologically detectable, but, more importantly, fibrin is structurally responsible for the disease pathophysiology in this model for this disorder.

Development of airway obstructive lesions containing fibrin in conducting airways has also been noted with authentic SM, regardless of route of entry, both in humans as well as in various animal models using either neat or ethanolic SM vapor to produce injury (Willems, J. L., 1989, *Ann Med Milit Belg* 3S:1-61). Since the early 1900's, human victims of mustard gas injury have been reported to contain 'fibrinous pseudomembranes' within their airways, at times resulting in death by suffocation from complete blockage of bronchial or tracheal passages by these 'pseudomembranes' (Eisenmenger, W. et al., 1991, *J Forensic Sci* 36:1688-1698). More recent reports of human SM exposures from the Iran-Iraq war (1984-1986) have given detailed descriptions of the deleterious effects of these airway casts, reporting death in 80% of patients needing intubation for respiratory insufficiency due to severe airway obstruction (Eisenmenger, W. et al., 1991, *J Forensic Sci* 36:1688-1698). These human reports correlate with the findings presented here, where a nose only inhalation model of SM-analogs in rats was used, with 'pseudomembranes' further defined as fibrin-containing casts of plastic bronchitis. In regards to other animal models, when ethanolic SM vapor was delivered to glass catheter-intubated rats, the same type of injury in the conducting airways occurred, with fibrin-containing casts present in the bronchi and bronchioles (Gao, X. et al., 2011, *Toxicol Pathol* 39:1056-1064). In the porcine SM model, where high dose SM was delivered as a neat vapor via nasal inhalation, gas exchange abnormalities mirroring these findings were noted, but more importantly, airway obstructive lesions caused mortality in 40% of the pigs in less than 6 hours from initial SM exposure (Fairhall, S. J. et al., 2010, *Inhal Toxicol* 22:1135-1143). Thus, an injury affecting the conducting airways has been reported in both humans and animal models of SM inhalation, found in the SM analog-inhalation model disclosed herein.

The selectivity for injury of the conducting airways with SM or CEES, particularly to the areas of bronchial (systemic) circulation, is of interest. While SM is more reactive and toxic than the SM analog, they both tend to cause injury very near their point of entry, with dissipation down the airways. It is believed that the more proximal conducting airways are injured because of a) a heightened bronchial circulation susceptibility to mustard injury, b) the highly reactive nature of the agent as it dissipates while traversing down the airways, and c) the size of particles created by either the SM analog aerosol or SM vapor is suitable for distribution in the affected airways. With respect to particle size in this disclosed model, the count median diameter for the SM analog-ethanolic aerosol is 0.6 micron, and the mass median diameter of the aerosol is 3.87 microns. This small particle size assures that the particles can reach all lung compartments, including both distal airways and alveoli. Certainly, a small amount of the SM analog-ethanolic particles can agglomerate and become deposited more proximally into the uppermost airways, as previous reported in a publication showing extensive nasal injury after SM analog inhalation (O'Neill, H. C. et al., 2011, *Am J Respir Cell Mol Biol* 45:323-331). Nevertheless, a pulmonary injury selective to the proximal conducting airways is the dominating feature of acute mustard inhalation, despite the ability of particles to reach and deposit within alveolar surfaces.

Disclosed herein, intratracheal administration of tPA completely eliminated SM and an SM analog exposure-related mortality from plastic bronchitis, even when rescue treatment was delayed almost 6 hours after injury, and yet was uniformly effective, provided that two consecutive doses were given once dosing was initiated. This effect despite delay of treatment is of important clinical relevance, because patients with plastic bronchitis often do not present early in their clinical course, but rather present to an acute care facility when their cast obstruction is severe enough to cause significant morbidity (such as respiratory distress and hypoxemia). Moreover, victims of sulfur mustard poisoning are often unaware that they have been exposed until several hours later, when skin blisters and respiratory symptoms arise as their airways begin to form obstructive bronchial casts. Thus, emergency medical care can be significantly delayed, and tPA treatment still be extremely effective as 'late rescue' therapy for any underlying cause of plastic bronchitis.

Dose-related improvements in multiple parameters related to CEES-inhalation injury after tPA treatment were noted. First, tissue oxygen delivery, as measured via pulse oximetry at 12 hours, was improved in a dose-dependent fashion. Second, dose-related reduction in percent airway obstruction by airway casts as assessed morphometrically during airway microdissection was detected. This effect was most profound with the highest tPA dose (0.7 mg/kg) used, and no bleeding side effects were observed. Third, dose-related reduction in clinical symptoms of respiratory distress was recognized, confirming the likely relationship between tissue oxygenation, airway obstruction by casts, and clinical respiratory distress. In addition, the Inventors also found a greatly beneficial effect of tPA treatment on pulmonary gas exchange and tissue acidosis. All tPA doses tested resulted in significant improvements of SM and an SM analog-associated gas exchange abnormalities (as reflected by normalization of $p_aO_2$, $P_aCO_2$, and arterial blood pH), while plasma lactate showed normalization only with the highest (0.7 mg/kg) dose. These non-uniform dose-related morbidity measure findings are most likely due to the varying severity of inadequate tissue oxygen delivery seen with lower tPA doses, corresponding to a lesser efficacy of cast lysis, and thus a diminished capacity for respiratory compensation at higher degrees of airway obstruction. Therefore, it is most likely that a threshold level of airway obstruction from casts exists, below which normal ventilation and arterial oxygenation is still maintained, while tissue perfusion is already compromised.

The following examples are provided for the purpose of illustration and are not intended to limit the scope of the present invention. Any variations which occur to the skilled artisan are intended to fall within the scope of the present invention. Each publication, sequence or other reference disclosed below and elsewhere herein is incorporated herein by reference in its entirety, to the extent that there is no inconsistency with the present disclosure.

EXAMPLES

Example 1

This example demonstrates that intratracheal administration of tPA diminishes airway fibrin-containing casts while improving clinical respiratory distress, pulmonary gas exchange, tissue oxygenation, and oxygen utilization in the disclosed model of severe chemically-induced plastic bronchitis. In addition, mortality, which was associated with hypoxemia and clinical respiratory distress, was eliminated.

In this example, adult rats exposed to sulfur mustard analog (CEES, 2-chloroethyl ethylsulfide; a sulfur mustard, abbreviated as SM for this example) were treated with intratracheal tPA (0.15-0.7 mg/kg, 5.5 hours and 6.5 hours after SM exposure), compared to controls (no treatment, isoflurane, and placebo). Respiratory distress and pulse oximetry were assessed (for 12 hours or 48 hours), and arterial blood gases were obtained at study termination (12 hours). Airway microdissection on fixed lungs was done to assess airway obstruction by casts. Optimal intratracheal tPA treatment (0.7 mg/kg) completely eliminated mortality (0% at 48 hours) and greatly improved morbidity in this nearly uniformly fatal disease model disclosed herein (90-100% mortality at 48 hour). tPA normalized plastic bronchitis-associated hypoxemia, hypercarbia, and lactic acidosis, and improved respiratory distress (i.e. decreased clinical distress scores) while decreasing airway fibrin casts.

Methods used in Example 1:

Chemicals 2-chloroethyl ethyl sulfide (CEES) was obtained from TCI America (Portland, Oreg.). Tissue plasminogen activator (tPA) was purchased from Genentech (Roche, San Francisco, Calif. and as disclosed in U.S. Pat. No. 5,612,029 incorporated herein by reference). All other chemicals were purchased from Sigma-Aldrich Chemical Co. (St. Louis, Mo.) unless otherwise indicated.

Animal Care

The Institutional Animal Care and Use Committee (IACUC) of National Jewish Health (NJH) center approved this study. Adult male (300-350 g) Sprague-Dawley rats (Harlan Co., Indianapolis, Ind.) were used.

Inhalation Exposure to CEES

CEES (10%) inhalation exposure was conducted as previously described (Veress, L. A. et al. 2010, *Am. J. Respir. Crit. Care Med.* 182:1352-1361). 10% CEES in ethanol was used exclusively in these experiments, in order to produce the desired level of injury. Briefly, anesthetized rats were placed in a nose-only inhalation system (CH Technologies, Westwood, N.J.), and were delivered the aerosolized CEES for 15 minutes, then removed from polycarbonate tubes, and observed until fully recovered from anesthesia.

Respiratory Distress Clinical Scoring

The respiratory distress clinical scoring criteria used were developed by the inventors and are specific for plastic bronchitis-induced respiratory distress in this rat model of CEES chemical inhalation. Respiratory quality, wheezing/stridor and activity depression were assessed (see Table 1) and agreed upon by 2 separate laboratory workers, and the individual scores (0 to 3) were added to obtain a cumulative score (max of 9). A score of 10 was given to rats that died prior to the conclusion of the experiment.

TABLE 1

RESPIRATORY CLINICAL DISTRESS SCORE CRITERIA

| SCORE | RESPIRATORY QUALITY | STRIDOR | ACTIVITY |
|---|---|---|---|
| 0 | Normal | Normal | Normal |
| 1 | Mild abdominal breathing with tachypnea (>100) | Stridor with activity only, mild | Mildly depressed activity |
| 2 | Moderate abdominal breathing, possibly with mild gasping | Stridor at rest, mild to moderate | Moderately depressed activity (movement with stimulation) |
| 3 | Severe abdominal breathing, severe gasping, and low respiratory rate (<60) | Stridor at rest, severe | Obtunded, no movement with stimulation; or severe agitation with stimulation |

Euthanasia Criteria

Animals were euthanized if oxygen saturation <70%, and respiratory distress score of 7 or greater. Euthanasia was performed using pentobarbital overdose (Sleepaway, Fort Dodge Animal Health, Fort Dodge, Iowa) (Veress, L. A. et al. 2010, Am. J. Respir. Crit. Care Med. 182:1352-1361). Animals were continuously monitored throughout experiments, and were euthanized prior to completion of experiment if institutional IACUC-approved euthanasia criteria were met. Euthanasia criteria were met if a rat had both: 1) oxygen saturation <70% (by a small animal pulse oximeter), and 2) respiratory clinical distress score >7. Animals were assessed for meeting euthanasia criteria by 2 observers, and if disagreement occurred, a third was asked for consultation.

Lung Fixation

Animals were euthanized at 12 hours after exposure as per experimental design, or if required prior to study termination. Tracheas were cannulated, and lungs were fixed at 20 cm H$_2$O with 4% paraformaldehyde in phosphate-buffered saline (PBS) for 30 minutes, and then surgically removed.

Airway Cast Scoring

Cast scoring was developed based on previously described microdissection techniques done by our group (Veress, L. A. et al. 2010, Am. J. Respir. Crit. Care Med. 182:1352-1361). Fixed lung was separated into five lobes by cross-sectioning each lobar bronchus at site of take-off from central airway bronchus (FIG. 1A). To obtain "main airway cast score", each lobe was positioned with main lobar bronchus perpendicular to microdissecting scope lens. A "dependent airway cast score" was also obtained for first major gravity-dependent lobar bronchi that were the most occluded in this model. To obtain this score, microdissection was performed to this first gravity-dependent (ventrally oriented) daughter branch, was then cross-sectioned at its take-off position (FIG. 1A, lines with arrows pointing at them), and then aligned perpendicularly under the dissecting scope. A digital picture was obtained of each lobar opening (FIG. 1C). An imaging program, IMAGE-J® (1.44p, NIH, USA) was used to assess percent airway occlusion from cast. To obtain a quantitative score, percent occlusion for each bronchus was converted to a nominal score, scale of 0 (no occlusion) to 7 (complete occlusion), (FIG. 1C), and each score was weighted based on volumetric differences of rat lobes to total lung (38)(raw score x % of lobar volume as to the whole/100) (Table 2). The five separate lobes' weighted scores were then added to obtain the "main" or "dependent" composite cast score for each animal (total score of 0 to 7).

TABLE 2

Weighted Cast Score Calculation

| Raw Lobar Cast score | % volume of lobe/total lung | Weighted lobar score |
|---|---|---|
| RUL score × | (10%/100) = | weighted RUL score |
| RML score × | (14%/100) = | weighted RML score |
| RLL score × | (28.5%/100) = | weighted RLL score |
| RA score × | (11%/100) = | weighted RA score |
| LL score × | (36.5%/100) = | weighted LL score |

Sum of individual weighted scores = Total weighted lung cast score
RUL = right upper lobe;
RML = right middle lobe;
RLL = right lower lobe;
RA = right accessory lobe;
LL = left lobe Noninvasive Oxygen Saturation Measurements A small animal oximeter (Starr Life Sciences, Oakmont, Pa.) in unanesthetized rats was used with XL CollarClip Sensor. An average value was recorded every five seconds using the oximeter software, and 3 of these readings were averaged to give a final value.

Arterial Blood Gas Measurements (ABG)

Arterial blood from descending aorta was collected (via 21 gauge butterfly catheter) and 100 µl was immediately placed into a pre-calibrated test card (EPOC-BGEM Test Card,) and analyzed using the EPOC-Vet Blood Analysis system (Epocal Inc., Ottawa, ON, Canada) at room temperature. Values for arterial pH, $P_aCO_2$, $p_aO_2$, bicarbonate, and lactate were assessed and reported.

Statistical Analysis

Prism 5.01 software (GraphPad, La Jolla, Calif.) was used, with one-way analysis of variance (ANOVA) plus Tukey's post-hoc analysis or Kruskal-Wallis plus Dunn's post-hoc analysis, depending on distribution of data. A p value <0.05 was significant.

Results

Optimal tPA Treatment Regimen Improves Survival

Figure 2:
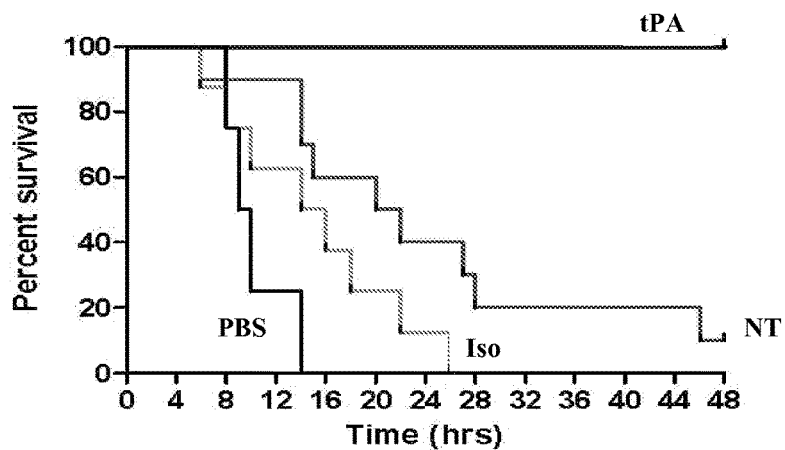
FIG. 2 shows the effect of tPA on mortality after sulfur mustard analog (2-Choloethyl ethyl sulfide; CEES) inhalation. Survival curves for rats exposed to CEES and given either: no treatment (NT, n=10); 'sham' treatment with isoflurane anesthesia only (Iso, n=8); placebo treatment (isoflurane anesthesia plus intratracheally administered phosphate-buffered saline (PBS, n=4); or 4) tPA treatment (isoflurane anesthesia plus intratracheally administered tPA, n=12). All three control groups had significantly lower survival than did rats given tPA treatment (p<0.0001 for Iso or PBS vs tPA, and p<0.001 for NT vs tPA, via Log-rank, Mantel-Cox test).

Survival over 48 hours after high level CEES (10%) inhalation in rats with and without intratracheal tPA (0.7 mg/kg) was measured. Three control groups were also evaluated. These included: 1) rats given no drug but exposed to CEES (NT), 2) rats receiving no drug treatment, exposed to CEES and given isoflurane anesthesia (Iso), and 3) rats given CEES exposure, isoflurane, and intratracheally delivered diluent for tPA (PBS, placebo). High level CEES exposure caused high mortality at 48 h in all control groups, including 90% mortality with NT, 100% with Iso, and 100% with PBS (FIG. 2). Remarkably, tPA completely eliminated mortality in this model. Deaths in control groups occurred mainly between 8 hours and 28 hours after CEES exposure. Sham/placebo (PBS) and sham treatment alone (Iso) both hastened mortality (see FIGS. 8A and 8B).

Figure 8A:
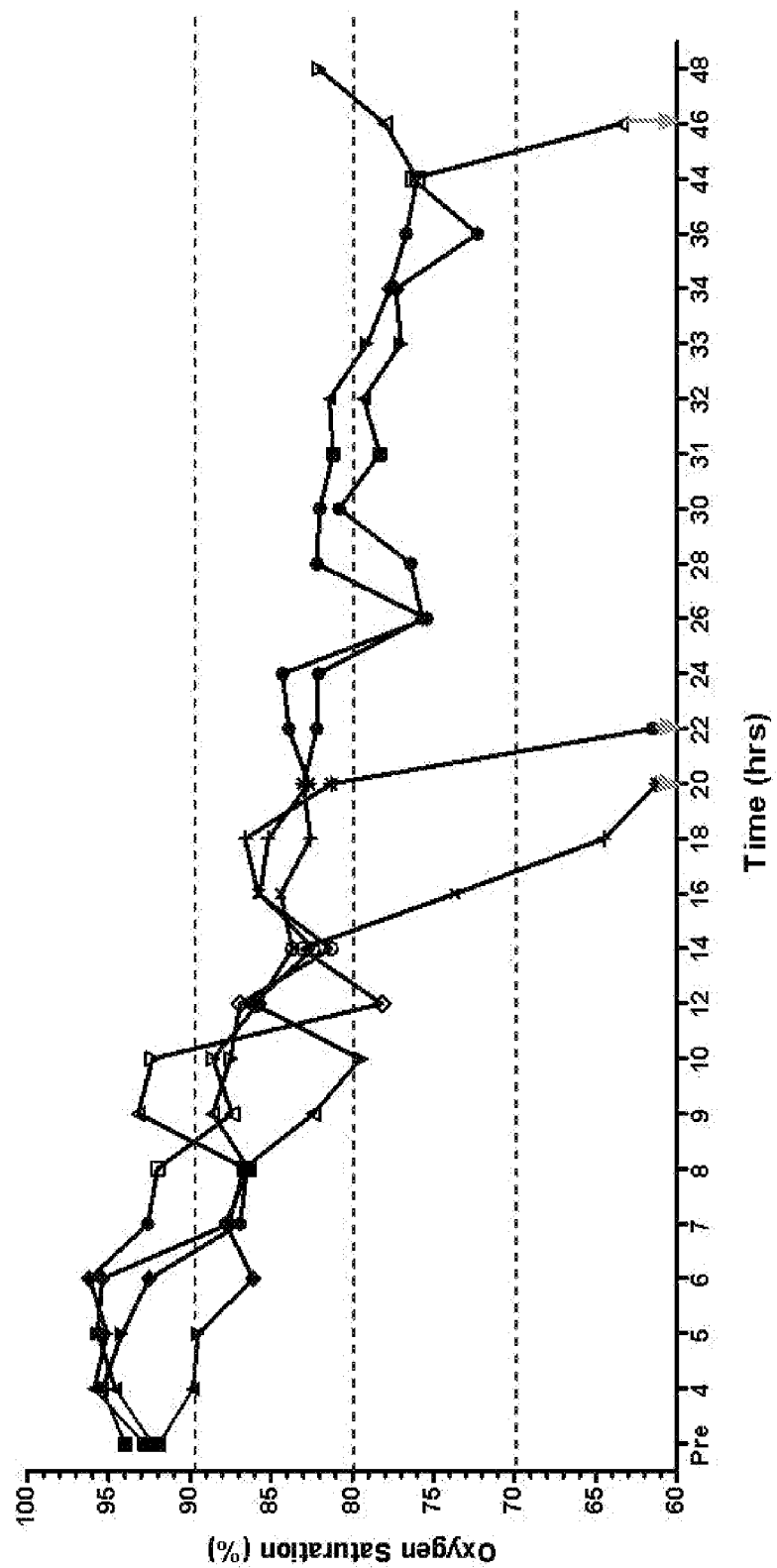
FIGS. 8A to 8D shows tissue oxygenation (SpO$_2$) measured by pulse oximetry in individual rats. Rats were given.
Figure 8B:
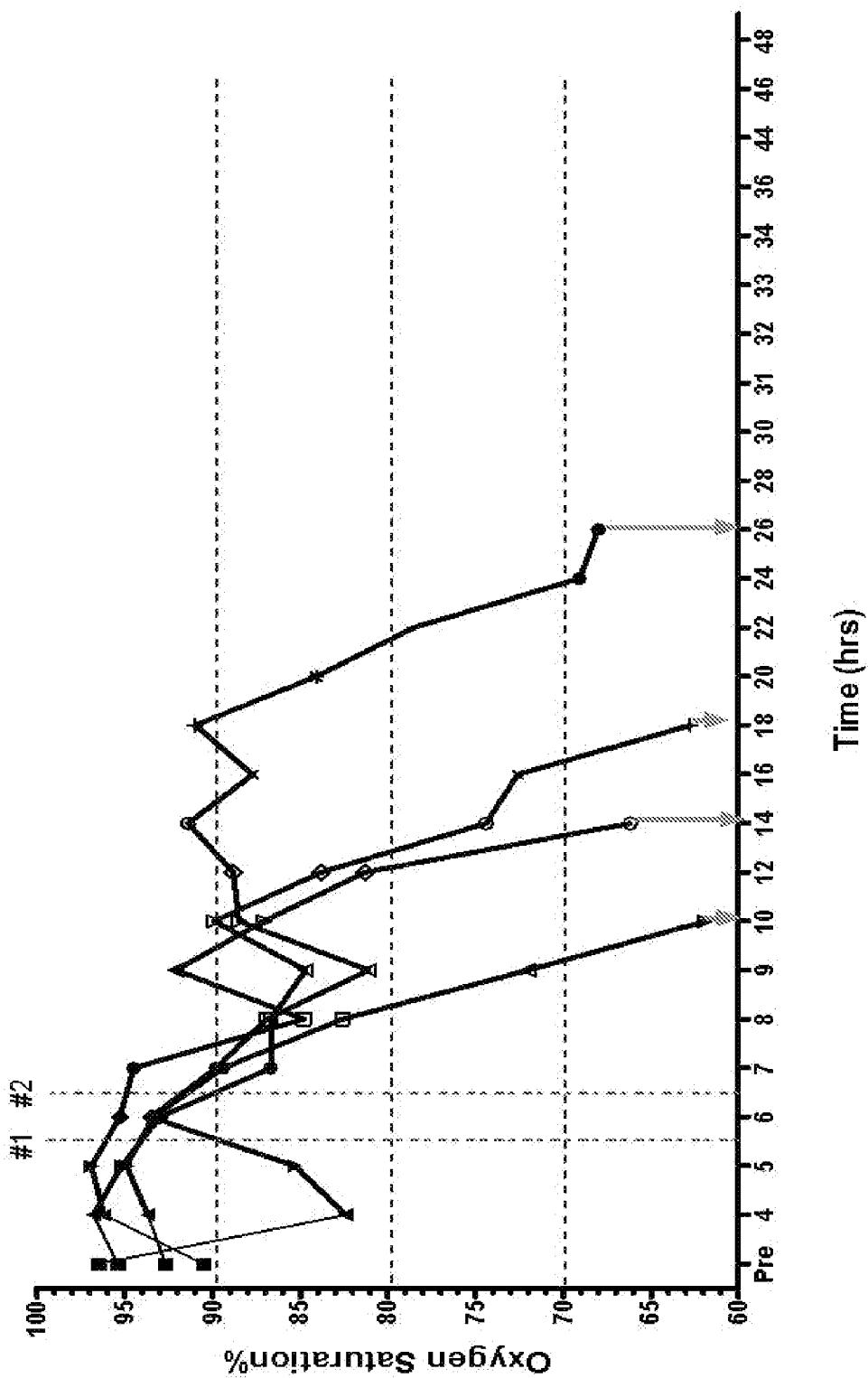
Figure 8C:
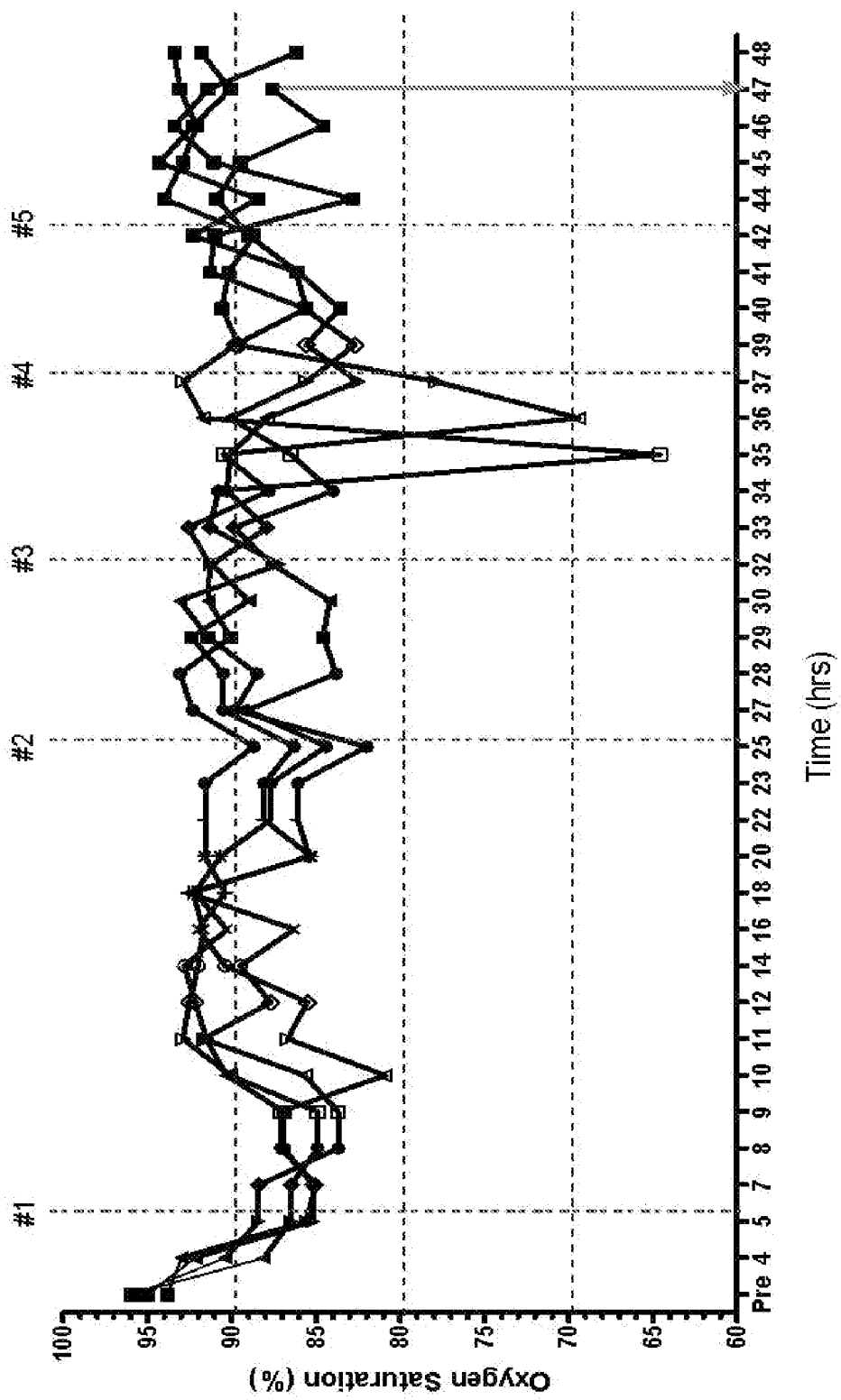
Figure 8D:
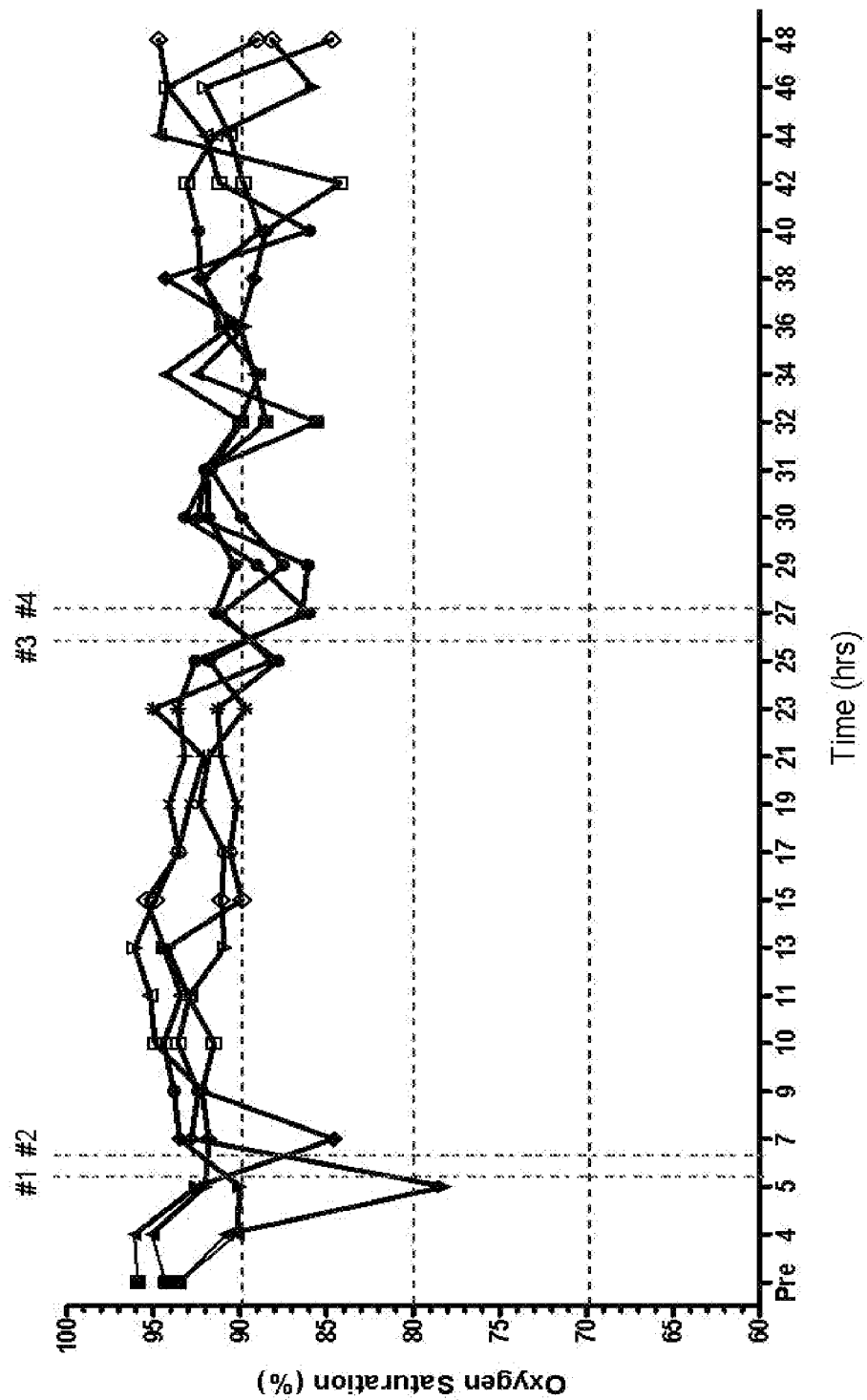
Figure 9:
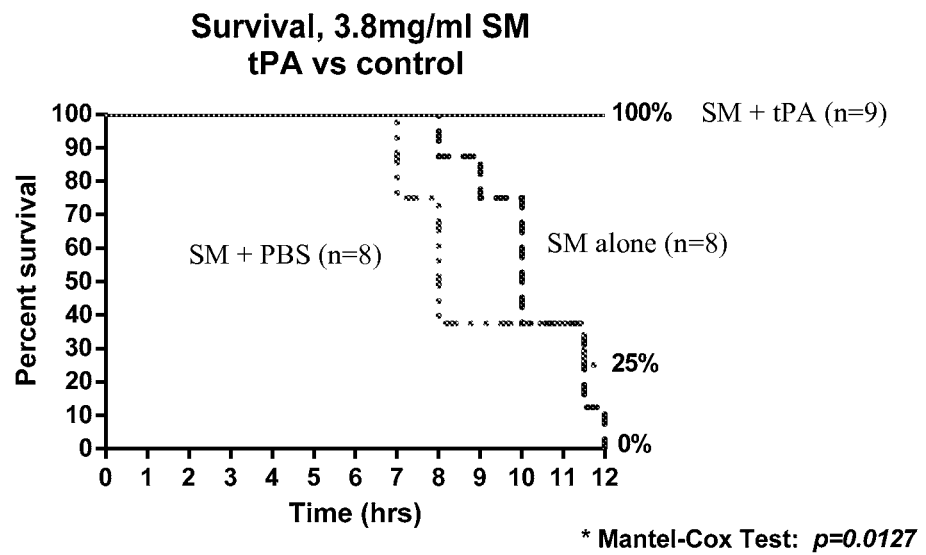
FIG. 9 shows the effect of tPA on mortality after sulfur mustard vapor inhalation. Survival curves for rats exposed to SM vapor (3.8 mg/kg) and given no treatment (SM alone, n=8, dashed line, going to 0% by 12 h), Placebo treatment (isoflurane anesthesia plus intratracheally administered phosphate-buffered saline (SM+PBS, n=8, dotted dashed line, going to 25% by 12 h), or tPA treatment (isoflurane anesthesia plus intratracheally administered tPA, SM+tPA, n=9; top line, staying at 100% by 12 h). Both control groups had significantly lower survival (0% with SM alone) than did rats given tPA treatment. (p=0.002 for PBS vs tPA, and p=0.003 for SM alone vs tPA, via Long-rank, Manel-Cox test)
Figure 10:
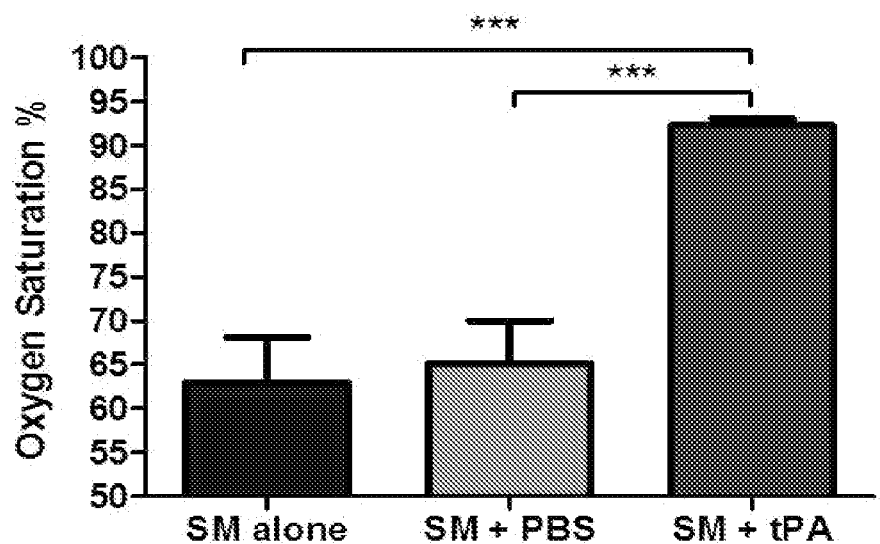
FIG. 10 shows the effect of tPA on tissue oxygenation in unanesthetized rats at time of euthanasia after SM vapor inhalation. Noninvasively acquired oxygen saturations (SpO$_2$) measured by pulse oximetry at time of euthanasia (at 12 h or earlier if euthanized early due to meeting euthanasia criteria) in rats exposed to SM (3.8 mg/kg) vapor and given no treatment (SM alone, n=8), isoflurane plus intratracheal PBS (SM+PBS, n=8), or isoflurane plus intratracheal tPA (SM+tPA) (0.7 mg/kg, n=9). Significant improvement in SpO$_2$ was noted with tPA relative to controls (***p<0.0001, ANOVA for repeated measures, with Tukey's post-hoc analysis) with tPA treatment group resulting in near baseline oxygen saturations (>90%) at time of euthanasia (12 h). Values represent mean SpO$_2$ with error bars for SEM.
Figure 11:
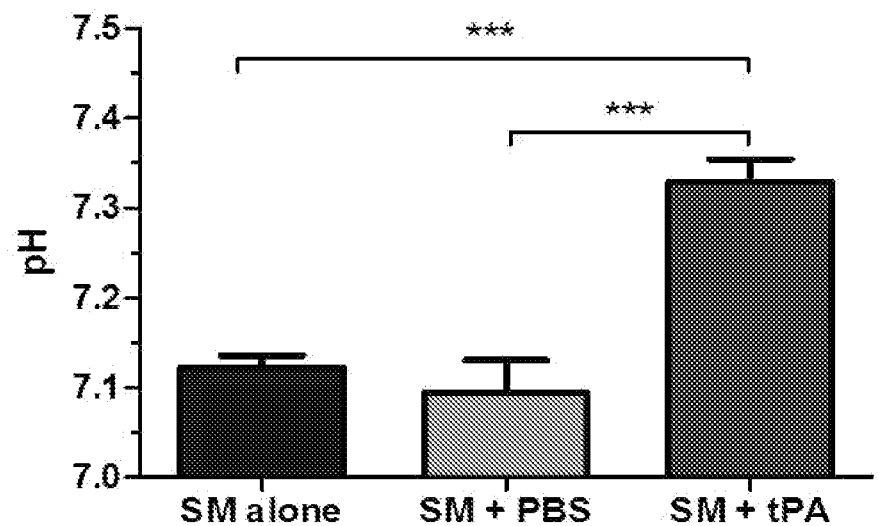
FIG. 11 shows the effect of tPA on tissue acidosis via the marker of arterial pH in rats at euthanasia after SM vapor inhalation. Arterial pH was measured in arterial blood via arterial blood gas (ABG) analysis at time of euthanasia (at 12 h or earlier if euthanized early due to meeting euthanasia criteria) in rats exposed to SM (3.8 mg/kg) vapor and given 1) no treatment (SM alone, n=5), 2) isoflurane plus intratracheal PBS (SM+PBS, n=8), or isoflurane plus intratracheal tPA (SM+tPA) (0.7 mg/kg, n=8). Significant improvement in arterial pH was noted with tPA relative to controls (***p<0.0001, ANOVA for repeated measures, with Tukey's post-hoc analysis) with tPA treatment group resulting in near baseline arterial pH (>7.30) at time of euthanasia (12 h). Values represent mean pH with error bars for SEM.
Figure 12:
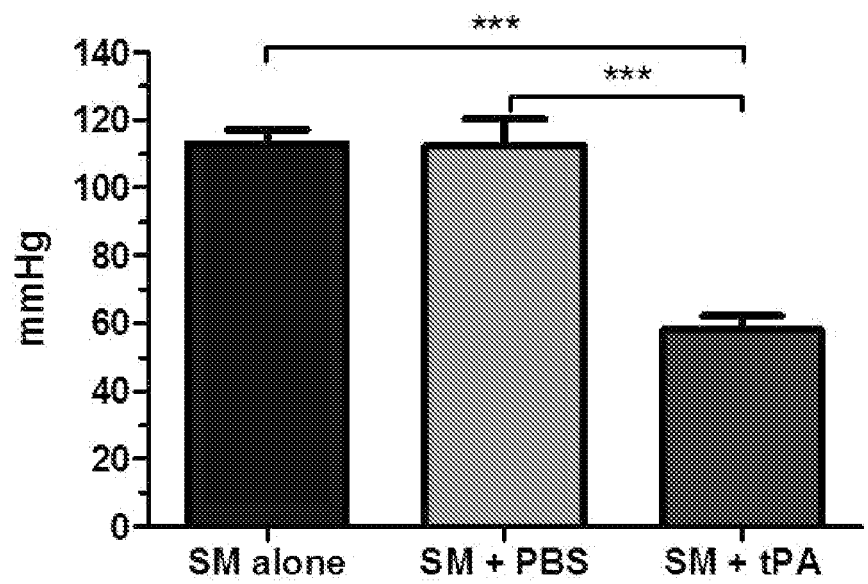
FIG. 12 shows the effect of tPA on ventilation marker of arterial P$_a$CO$_2$ in rats at time of euthanasia after SM vapor inhalation. Arterial P$_a$CO$_2$ was measured in arterial blood via arterial blood gas (ABG) analysis at time of euthanasia (at 12 h or earlier if euthanized early due to meeting euthanasia criteria) in rats exposed to SM (3.8 mg/kg) vapor and given 1) no treatment (SM alone, n=5), 2) isoflurane plus intratracheal PBS (SM+PBS, n=8), or isoflurane plus intratracheal tPA (SM+tPA) (0.7 mg/kg, n=8). Significant improvement in arterial P$_a$CO$_2$ was noted with tPA relative to controls (***p<0.0001, ANOVA for repeated measures, with Tukey's post-hoc analysis) with tPA treatment group resulting in near baseline arterial P$_a$CO$_2$ (<60 mmHg) at time of euthanasia (12 h). Values represent mean P$_a$CO$_2$ with error bars for SEM.
Figure 13:
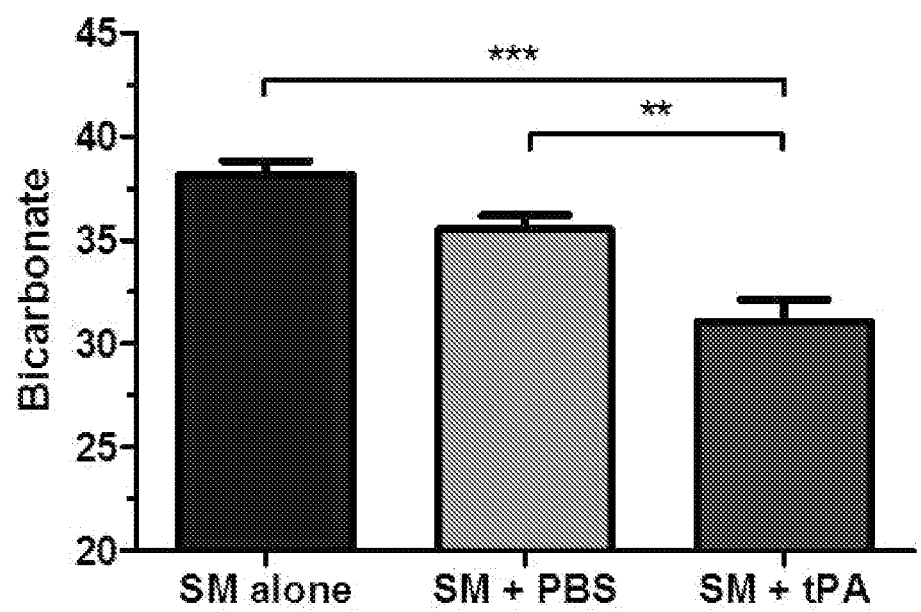
FIG. 13 shows the effect of tPA on arterial bicarbonate in rats at time of euthanasia after SM vapor inhalation. Arterial bicarbonate was calculated via arterial blood gas (ABG)

Initial tPA dosing was delayed until 5.5 hours after exposure. This dosing time was based on previous observations that: 1) casts begin to form in airways at 4 hours (Veress, L. A. et al. 2010, Am. J. Respir. Crit. Care Med. 182:1352-1361), and 2) oxygen saturations decreased below 90% at 5 hours after exposure (FIG. 8A). Experiments indicated that a second tPA dose 1 hour after initial dosing was superior to only one dose, with consistently greater improvement in oxygen saturation (>90% within <1 hour with two doses, vs 6 hours with one dose); more consistently satisfactory oxygenation; higher peak oxygen saturation shortly after administration (96% with 2 doses, vs 92% with one); and elimination of mortality only with two initial doses (FIGS. 8C and 8D). Re-dosing of tPA was done using a similar two-dose regimen, with drug re-administration when oxygen saturation reached 85% and clinical distress worsened. Again, the two-dose regimen (1 h apart) was superior to only one dose given at re-dosing. In summary, the optimal two-dose tPA regimen (0.7 mg/kg, given twice), administered intratracheally, was highly effective, completely eliminating mortality.

Oxygen Saturation Improves with tPA Treatment

Figure 3:
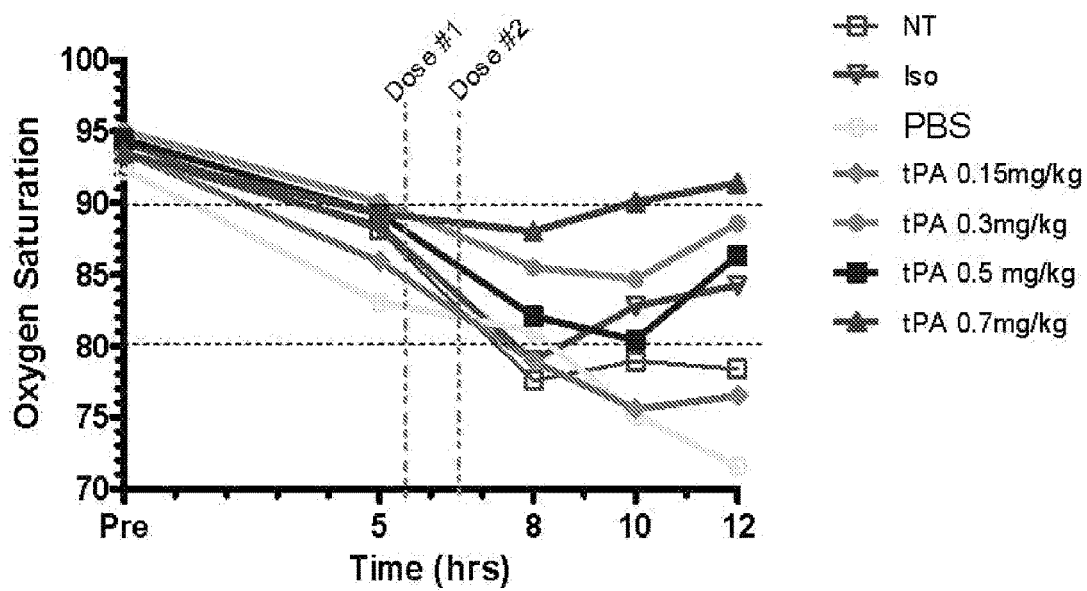
FIG. 3 shows the effect of tPA on tissue oxygenation in unanesthetized rats for 12 h after CEES inhalation. Noninvasively acquired oxygen saturations ($SpO_2$) were measured by pulse oximetry over 12 hours in rats exposed to CEES and given no treatment (NT, n=16); isoflurane anesthesia (Iso, n=10); isoflurane plus intratracheal PBS (PBS, n=4); or isoflurane plus intratracheal tPA at 0.15 mg/kg (n=6); 0.3 mg/kg (n=6); 0.5 mg/kg (n=6); or 0.7 mg/kg (n=16) doses. Vertical dashed lines indicate time interval during which the initial anesthetic, with tPA or PBS placebo, was administered (5.5 and 6.5 h). A dose-dependent improvement in SpO$_2$ was noted with tPA relative to controls (p=0.0003), with only the highest tPA (0.7 mg/kg) used resulting in near baseline oxygen saturations (>90%) at 12 hours. Values represent mean SpO$_2$, analyzed by ANOVA for repeated measures, with Tukey's post-hoc analysis. (See Table 3 detailed data)

A dose-effect of intratracheal tPA on oxygen saturation ($SpO_2$) in rats with plastic bronchitis after CEES inhalation was determined. Four tPA doses (0.15 mg/kg, 0.3 mg/kg, 0.5 mg/kg and 0.7 mg/kg) were tested and given as a one-time two-dose regimen at 5.5 hours and 6.5 hours, followed by pulse oximetry at 12 hours. A dose-dependent improvement was detected in $SpO_2$ with tPA treatment as compared to all three controls tested (FIG. 3). Improvement was noted within 2 hours after giving tPA, with $SpO_2$ measurements in tPA groups progressively diverging from controls over the next 4 hours. Optimal oxygenation occurred with 0.7 mg/kg tPA, with improved mean $SpO_2$ at 12 hours versus controls (mean $SpO_2$ of 91.4% in 0.7 mg/ml tPA group, vs. 78.4% in NT-CEES alone group; p=0.025) (Table 3). Improved $SpO_2$ also occurred with 0.3 mg/kg and 0.5 mg/kg, but to a lesser extent (mean $SpO_2$ of 88.6% and 86.4%, respectively). There was no improvement detected in oxygenation versus controls with 0.15 mg/kg. However, an impressive survival benefit was seen at 12 hours with every tPA dose. No mortality was observed at 12 hours in all tPA groups, versus 12.5% with NT, 30% with Iso, and 75% with PBS. PBS and Iso accelerated mortality. Due to high mortality in controls, $SpO_2$ data collected at 12 hours in controls (particularly PBS) contained only data from rats remaining alive (i.e. least affected by CEES exposure). Therefore, oxygenation data reported at 12 hours under-represents the real morbidity of this injury. Nevertheless, tPA remarkably corrected $SpO_2$ at 12 hours in a dose-dependent fashion relative to surviving controls.

Figure 4A:
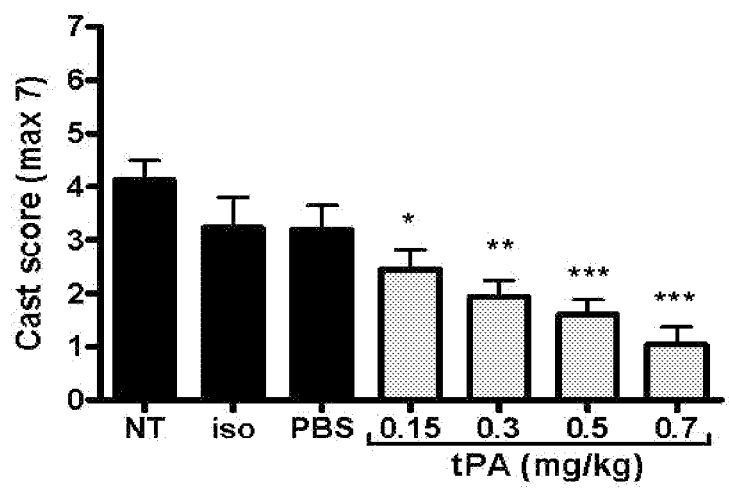
FIGS. 4A and 4B show the effect of tPA on airway obstruction by fibrin-containing casts at 12 hours after CEES inhalation. Casts were revealed by airway microdissection of Main Bronchi (FIG. 4A) and First Dependent Bronchi (FIG. 4B) (gravity dependent) of all lobes. Airway obstruction in rats given no treatment (NT) or placebo (Iso or PBS) was significantly different than that observed at any dose of tPA (p<0.0001 for both Main and First Dependent Bronchi), with a dose-dependent improvement in obstruction found with tPA. Values represent means±SEM, with data analyzed by ANOVA, followed by Tukey's post hoc analysis; *p<0.05; p=<0.01; *p<0.001 denoting significance relative to NT. (n=6 for all groups, except Iso and PBS where n=3).
Figure 4B:
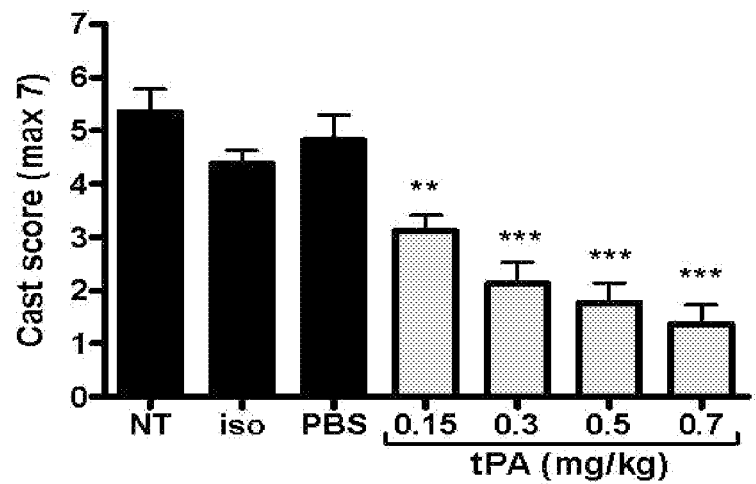

Bronchi were compared from four tPA treatment groups (0.15-0.7 mg/kg, given at 5.5 hours and 6.5 hours) with three control groups (NT, Iso, PBS). Lungs from animals euthanized at any point during study were included. tPA treatment greatly decreased airway obstruction by fibrin casts in a dose-dependent fashion (FIGS. 4A and 4B, respectively). No airway bleeding or pulmonary hemorrhage was noted at necropsy in any tPA-treated animals. Cast scores amongst the three control groups were not different, with each being greatly elevated. Controls showed a mean Main Bronchi cast score of >3.2 (corresponding to >46% total airway occlusion by casts), and a mean First Dependent Branch cast score of >4.4 (corresponding to >63% total airway occlusion). The greatest reduction of cast scores was noted with 0.7 mg/kg tPA, where a 4-fold reduction occurred in both Main Bronchi cast scores (score of 1.3) and First Dependent Branch cast scores (score of 1.0) compared to controls (p<0.001). With 0.5 mg/kg tPA, we found a 3-fold reduction in both Main and Dependent Bronchi cast scores (scores of 1.6 and 1.7, respectively; p<0.001), while with the 0.3 mg/kg dose we found a 2.5-fold reduction in these two respective scores (scores of 1.9 and 2.1, with p<0.001 and p<0.01, respectively). The 0.15 mg/kg tPA dose was less effective. An individual Main Branch cast score of >3.5 (corresponding to a >50% total airway occlusion) was associated with non-survival. Indeed, all rats dying before 12 hours had very severe airway obstruction by casts, ranging from cast scores of 3.5 to 5.7 (50 to 81% total airway occlusion). Thus, optimal tPA treatment had a remarkable effect in decreasing airway obstruction by fibrin casts.

Respiratory Clinical Scoring Improvement after tPA Administration

The inventors developed a clinical respiratory distress scoring system, based upon signs of distress in rats due to plastic bronchitis, including: 1) respiratory quality (i.e. work of breathing), 2) level of activity, and 3) degree of stridor (Table 1). The three higher tPA doses tested, but not 0.15 mg/kg, significantly improved respiratory clinical scores at

TABLE 3

Oxygen Saturation with CEES Inhalation Plus tPA vs. Controls

| CEES + treatment | Pre-exposure (%)* | 5 h (%)* | 8 h (%)* | 10 h (%)* | 12 h (%)* | Mortality |
|---|---|---|---|---|---|---|
| NT | 94.1 ± 0.4<br>n = 16 | 88.1 ± 1.6<br>n = 16 | 77.6 ± 1.7<br>n = 15 | 78.9 ± 2.4<br>n = 14 | 78.4 ± 3.2<br>n = 14 | 12.50% |
| Iso | 93.5 ± 0.6<br>n = 10 | 88.4 ± 2.4<br>n = 10 | 79.0 ± 4.8<br>n = 9 | 82.8 ± 3.8<br>n = 8 | 84.3 ± 2.7<br>n = 7 | 30% |
| PBS | 92.4 ± 1.2<br>n = 4 | 83.1 ± 1.7<br>n = 4 | 81.1 ± 3.1<br>n = 4 | 75.2 ± 11.6<br>n = 2 | 71.6 ± 0<br>n = 1 | 75% |
| 0.15 mg/mL tPA | 93.5 ± 0.5<br>n = 6 | 85.9 ± 0.8<br>n = 6 | 79.0 ± 3.1<br>n = 6 | 75.6 ± 3.8<br>n = 6 | 76.5 ± 2.6<br>n = 6 | 0% |
| 0.3 mg/mL tPA | 95 ± 0.4<br>n = 6 | 90.1 ± 1.3<br>n = 6 | 85.5 ± 2.3<br>n = 6 | 84.7 ± 2.7<br>n = 6 | 88.6 ± 0.9<br>n = 6 | 0% |
| 0.5 mg/mL tPA | 94.4 ± 0.6<br>n = 6 | 89.2 ± 2.2<br>n = 6 | 82.1 ± 2.4<br>n = 6 | 80.5 ± 2.5<br>n = 6 | 86.4 ± 1.3<br>n = 6 | 0% |
| 0.7 mg/mL tPA | 93.4 ± 0.3<br>n = 16 | 89.3 ± 1.2<br>n = 16 | 88.0 ± 0.9<br>n = 16 | 90.1 ± 1.0<br>n = 16 | 91.4 ± 0.9<br>n = 16 | 0% |

Figure 5:
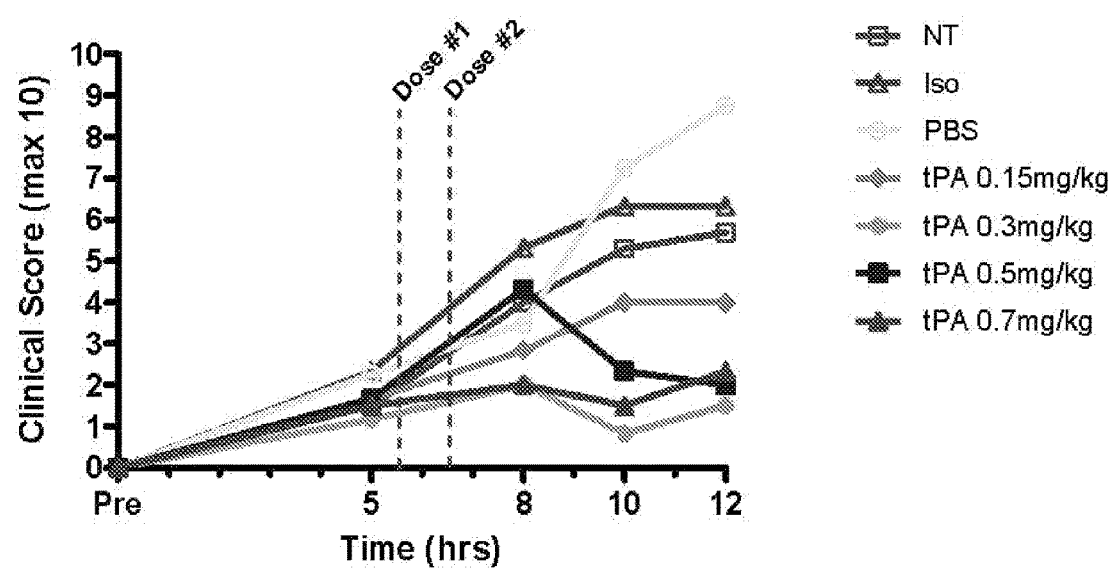
FIG. 5 shows the effect of tPA on respiratory distress for 12 hours after CEES inhalation. Respiratory Clinical Distress was scored on basis of quality of respirations (0-3), stridor (0-3), and physical activity (0-3), with highest numbers indicating more severe clinical distress (see Table 1 for further details). Respiratory Clinical Scores for the groups given the highest three tPA doses (>0.3 mg/kg) were significantly different from each of the three control groups (p=0.004), while 0.15 mg/kg tPA did not differ from controls. Values represent mean clinical scores, analyzed by ANOVA for repeated measures, with Tukey's post-hoc analysis. (n=10 in NT, n=3 for PBS, n=4 for Iso, and n=6 for all tPA groups.) (See Table 3 detailed data.) Vertical dashed lines indicate time interval during which the initial anesthetic, with tPA or PBS placebo, was administered (5.5 and 6.5 h).

*Values shown are mean ± SEM
NT = no treatment control (CEES alone)
Iso = isoflurane control
PBS = phosphate buffered saline control Reduction of Airway Obstruction by Fibrin Casts with tPA Treatment The effects of tPA on fibrin casts within airways was assets. The inventors developed a quantitative scoring system of total airway obstruction by casts (FIG. 1B). 12 hour composite cast scores from Main and First Dependent 12 hours versus controls (p=0.004; FIG. 5). While controls had greatly elevated clinical scores of >5.7 at 12 hours (on scale of 0-10, higher scores implying worse distress), clinical scores with tPA (0.3 mg/kg and above doses) were <2.3, which is a 2.5-fold reduction in distress. Moreover, these higher tPA dose groups had 12 h clinical scores (all <2.3)

near baseline (pre-exposure) levels. Meanwhile, the controls (NT, Iso, PBS) and 0.15 mg/kg tPA group had progressively worsening scores over 12 hours. All significantly differed from baseline (zero) by the conclusion of the experiment (5.7 for NT, p<0.0001; 6.3 for Iso, p=0.0009; 8.8 for PBS, p<0.0001; and 4.0 for 0.15 mg/kg tPA, p=0.008) (Table 4). The placebo (PBS) group had the worst mean clinical score at 10 and 12 hours, representing the group with the greatest distress or clinical morbidity. Intratracheal tPA, at higher doses, was quite beneficial in reducing clinical distress.

TABLE 4

Respiratory Distress Scores with CEES Inhalation, Plus tPA vs. Controls

| CEES + treatment | Pre-exposure | 5 h | 8 h | 10 h | 12 h | Significance# (Pre to 12 h) |
|---|---|---|---|---|---|---|
| NT | 0 | 1.5 ± 0.2 | 4.0 ± 0.7 | 5.3 ± 0.8 | 5.7 ± 0.8 | p < 0.0001 |
| Iso | 0 | 2.3 ± 0.9 | 5.3 ± 1.5 | 6.3 ± 2.0 | 6.3 ± 1.9 | p = 0.0009 |
| PBS | 0 | 2.3 ± 0.9 | 3.5 ± 0.9 | 7.3 ± 1.5 | 8.8 ± 1.2 | p < 0.0001 |
| 0.15 mg/mL tPA | 0 | 1.6 ± 0.2 | 2.8 ± 0.6 | 4.0 ± 0.8 | 4.0 ± 0.9 | p = 0.008 |
| 0.3 mg/mL tPA | 0 | 1.2 ± 0.2 | 2 ± 0.3 | 0.8 ± 0.3 | 1.5 ± 0.4 | ns |
| 0.5 mg/mL tPA | 0 | 1.7 ± 1.2 | 4.3 ± 0.7 | 2.3 ± 0.6 | 2.0 ± 0.7 | ns |
| 0.7 mg/mL tPA | 0 | 1.5 ± 0.2 | 2.0 ± 0.4 | 1.5 ± 0.3 | 2.3 ± 0.6 | ns |

Figure 6A:
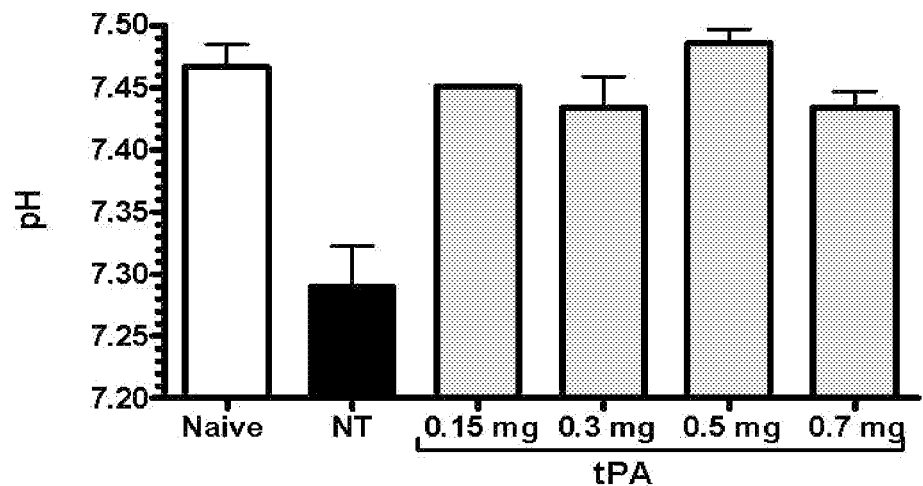
FIGS. 6A-6D show the effect of tPA on pulmonary gas exchange via arterial blood gas (ABG) measurements in rats 12 h after CEES inhalation. Data for (FIG. 6A) arterial pH, (FIG. 6B) p$_a$CO$_2$, (FIG. 6C) bicarbonate, and (FIG. 6D) p$_a$O$_2$ were compared in rats given tPA versus those given no treatment (NT), and naïve (air breathing) rats at altitude, 5292 ft, barometric pressure 624 mmHg (Denver, Colo.). All tPA doses effectively normalized CEES-induced acidosis (p=0.026), hypercarbia (p=0.016), and hypoxemia (p=0.041) at 12 hours. Values represent means±SEM (n=4 per group, except in 0.15 mg/kg tPA where n=2). Data were analyzed using Kruskal-Wallis test for not normally distributed data.
Figure 6B:
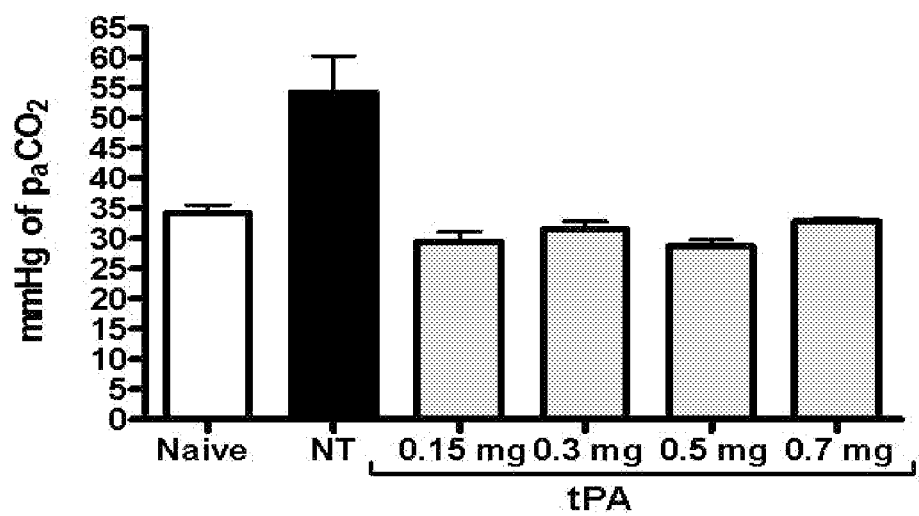
Figure 6C:
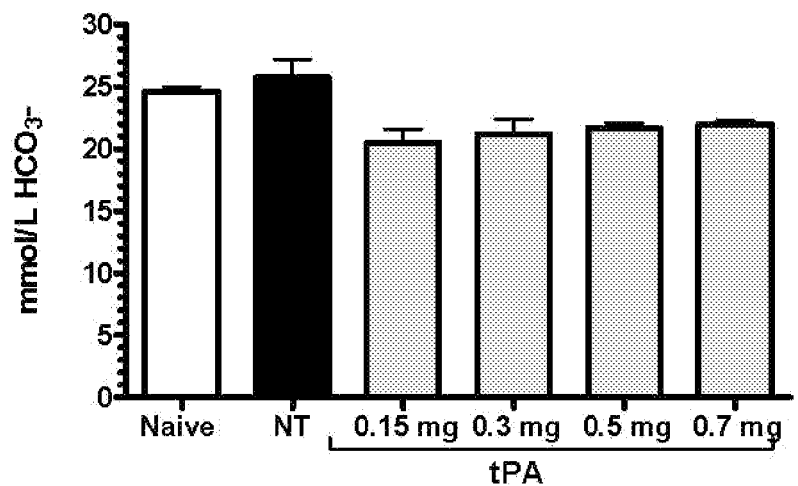
Figure 6D:
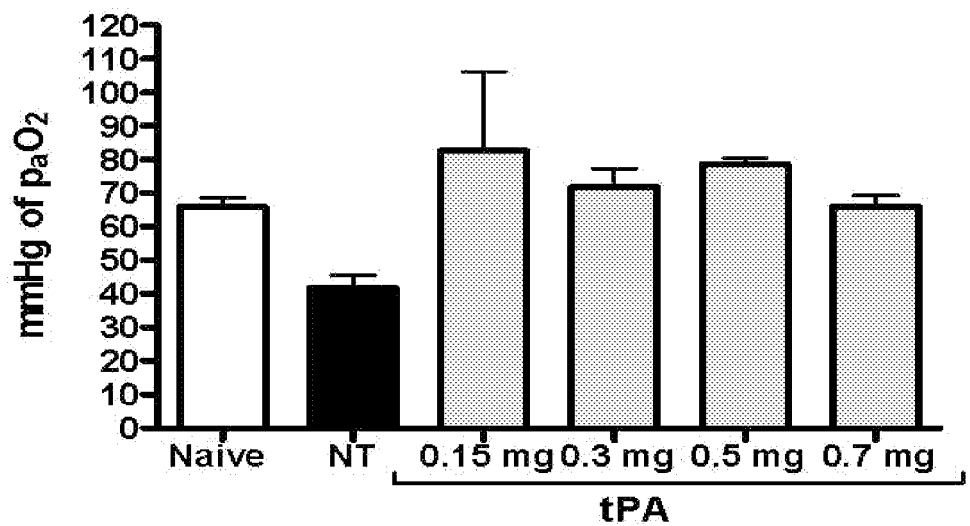

*Values shown are mean ± SEM
Statistical analysis by ANOVA, with Tukey's post-hoc analysis
ns = not significant
NT = no treatment control (CEES alone)
Iso = isoflurane control
PBS = phosphate buffered saline control tPA Normalizes Arterial Blood Gas (ABG) Abnormalities ABGs were obtained 12 hours after CEES exposure in rats receiving escalating tPA doses (0.15-0.7 mg/kg) at 5.5 hours and 6.5 hours, and compared these results to those from an untreated CEES-exposed group (NT), as well as an unexposed naïve group (at an altitude of 5292 ft, barometric pressure 624 mmHg, FIGS. 6A-6D). CEES exposure caused significant acidosis by 12 hours (mean pH of 7.29 in NT vs. 7.47 in naives, p=0.004), and all doses of tPA normalized pH levels to >7.4 (p=0.026; FIG. 6A). CEES exposure also impaired ventilation, resulting in elevation of $P_aCO_2$ (mean $P_aCO_2$ of 54 mmHg in NT vs. 34 mmHg in naives, p=0.012). All tPA doses improved ventilation ($p_aCO_2$ means <33 mmHg, p=0.016; FIG. 6B). While bicarbonate ($HCO_3-$) levels appeared normal with NT (mean $HCO_3-$ of 25.7 mmol/L), all tPA groups had a slight decrease in mean $HCO_3-$ (20.5-21.9 mmol/L, p=0.024; FIG. 6C). Invasive arterial oxygenation measurements via $p_aO_2$ analysis confirmed earlier noninvasive SpO$_2$ findings with decreased $p_aO_2$ levels at 12 h due to CEES inhalation (mean $p_aO_2$ of 42 mmHg in NT vs. 66 mm Hg in naives, p=0.003). Impressively, all tPA treatments, regardless of dose, returned $p_aO_2$ levels to those comparable to naïve animals ($p_aO_2$ means >66 mm Hg in all tPA groups, p=0.041; FIG. 6D).

Figure 7:
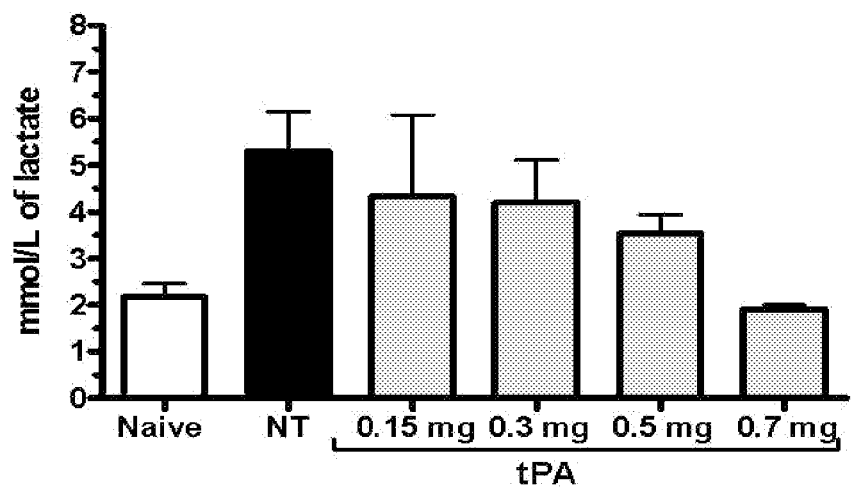
FIG. 7 shows the effect of tPA on tissue acidosis marker of arterial blood lactate at 12 hours after CEES inhalation. Data for lactate were compared in rats given tPA versus no treatment (NT), as well as naïve (air breathing) rats. An inverse dose-relationship between blood lactate and tPA dose was noted (p=0.016), with only the highest 0.7 mg/kg tPA normalizing lactate back to naïve levels. Values represent means±SEM (n=4 per group, except in 0.15 mg/kg tPA where n=2). Data were analyzed using Kruskal-Wallis test for not normally distributed data.

A dose-dependent improvement in blood lactate levels with tPA was also detected (FIG. 7). CEES exposure caused an increase in lactate by 12 hours compared to naïve levels (mean lactate of 6.5 mmol/L in NT, vs 2.1 mmol/L in naives, p=0.011). tPA (0.7 mg/kg) was able to normalize lactate completely (mean lactate of 1.9 mmol/L, p=0.006), while lesser doses of tPA were progressively less effective at correcting this marker of tissue acidosis (lactate means of 3.5, 4.3 and 4.4 mmol/L with 0.5, 0.3 and 0.15 mg/kg tPA, respectively). In summary, while ABGs were substantially improved by any tPA dose tested, the metabolic acidosis marker lactate was only optimally improved at the highest tPA dose (0.7 mg/kg). Elevated plasma lactate (lactic acid) is a reasonable surrogate for poor tissue oxygenation and/or perfusion.

Example 2

This example demonstrates that tissue plasminogen activator (tPA) increases survival thus preventing death following sulfur mustard (SM) vapor exposure.
Methods used in Example 2:

Sprague-Dawley rats (250 g), intubated, under anesthesia, inhaled a fatal dose of SM ethanolic vapor (3.8 mg/kg), resulting in death by 12 hours with no treatment. Pulse oximetry (pOx) measurements were obtained every one hour, with concurrent scoring of respiratory distress. Treatment group received tPA intratracheally (0.7 mg/kg in 50 µl, 2 doses q 1 h, n=9) under isoflurane anesthesia when pOx was below 85% (at 5 h). Two control groups were also evaluated [placebo (PBS-diluent n=8) and untreated but SM-exposed (NT, n=8)]. Re-dosing was performed when pOx decreased <85% again. Arterial blood gases (ABGs) were obtained at euthanasia, and cast scoring (airway obstruction scoring system) was performed on fixed lungs by microdissection.
Results By 12 hours, mortality from SM exposure alone (NT) was 100% (median survival: 10 hour), and with placebo-treatment was 75% (median survival: 8 hours). Rescue treatment with tPA resulted in 0% mortality, as all animals survived. Moreover, pOx at euthanasia in tPA-treated animals was significantly greater versus controls (mean±SEM: 92.3±0.8% with tPA; 63.0±5.1% with NT; 65.1±4.9% with placebo). ABG measurements at euthanasia were also greatly improved, showing recue from SM-induced respiratory failure and ventilation defects ($p_aCO_2$, mean±SEM, mmHg: 57±4 with tPA; 113±4 with NT; 112±8 with placebo), as well as rescue from SM-induced arterial acidosis (mean pH: 7.32±0.02 with tPA; 7.12±0.01 with NT; 7.09±0.04 with placebo). Serum bicarbonate was also significantly improved. Moreover, tPA treatment resulted in a greatly reduced airway fibrin cast burden, and thus prevented airflow obstruction. FIGS. 9-13 show these results.

High level SM inhalation causes significant mortality due to progressive respiratory failure from airway obstructing fibrin casts. Airway administration of tPA 5 hours after exposure prevented death due to SM inhalation in the rat. Moreover, tPA normalized both oxygenation and ventilation defects seen due to high level SM inhalation, thereby rescuing from respiratory distress and failure. Intra-airway tPA should be considered as a life-saving rescue therapy for human patients after a significant SM inhalation exposure incident.

Example 3

This example demonstrates that the administration of intratracheal tPA over a 48 hour period after inhaling a lethal quantity of sulfur mustard SM (3.8 mg/kg) diminishes airway fibrin-containing casts while improving clinical respiratory distress, pulmonary gas exchange, tissue oxygenation, and oxygen utilization. In addition, mortality, which was associated with hypoxemia and clinical respiratory distress, was eliminated.

Procedural design for Example 3 is shown in FIG. 14. Rats were exposed and then monitored by pulse oximetry and clinical examination hourly until randomization (oxygen saturation <85%, or >10% drop from baseline of ~97% at sea level) to either of 3 groups: 1) SM+no treatment (NT, or SM alone, n=12), 2) SM+placebo (PBS, n=13), or 3) SM+tPA treatment (n=9). Animals were then monitored every 2 hours after induction treatment dose, and were given a maintenance tPA (or PBS) treatment dose every 4 hours. All rats given intratracheal tPA or PBS received this by direct intratracheal instillation via an atomizer placed through the vocal cords into the mid-trachea by direct laryngoscopy under isoflurane anesthesia. Rats were monitored continuously for 48 hours for distress, euthanasia criteria assessment, and periodic (q2 h-every 2 hours) pulse oximetry/clinical distress scoring assessments.

Pulse oximetry values (estimated arterial oxygen saturation) in each group (i.e. SM+no treatment (NT, or SM alone, n=12); SM+placebo (PBS, n=13); or SM+tPA treatment (n=9)) was determined at the time of randomization. None were statistically different from the other (median of ~81%) (FIG. 15).

The survival of rats in each group noted above over the 48 hour study period was determined. Survival curves for rats exposed to SM (3.8 mg/kg) and given: 1) SM alone (referred to as Sm alone (n=12), 2) SM+PBS (referred to as SM/placebo (n=13)), or 3) SM+tPA treatment (referred to as SM/tPA (n=9)) is shown in FIG. 16. Both control groups (SM alone and SM/PBS) had 0% survival at 48 hours, while tPA treatment (SM/tPA) had 100% survival (p<0.0001, Log-rank, Mantel-Cox test). tPA treatment completely eliminated mortality (48 hours) after sulfur mustard (SM) inhalation, with no deaths within the 48 hour period, in contrast to 100% mortality in both SM alone and SM/PBS treated control groups (median time to death was 8 hours in SM alone group, and 9 hours in PBS treated group). Rats were electively euthanized per institutional IACUC protocol when they had sustained oxygen saturations below 70% in association with a clinical score of 7 or greater (9 being maximally severe, as indicated by severity of respiratory distress and inactivity). Our previous studies had demonstrated that rats exposed to SM do not recover or survive after reaching this level of sustained hypoxemia and distress.

The mean±SEM pulse oximetry values for the rats was tracked in the three treatment groups defined above from the time of randomization as shown in FIG. 17. Those given no treatment (SM alone referred to as "NT") all died within 2 hour of randomization, while placebo treated animals (referred to as "PBS") died within a few hours thereafter. In contrast, tPA treated animals (referred to as "tPA") given PBS after their initial dosing, showed a more gradual decline in pulse oximetry results. tPA treatment resulted in saturation improvement from nadir of <84% to near 90% after the first induction dose, with continued overall saturations >90-92% for the remainder of the study (to 48 hours). In addition, pulse oximetry results from exposure (time 0) for 48 hours in tPA versus controls after SM exposure was also determined. The data is from the time of exposure, and not from randomization, thereby each animal receiving therapies at different times. tPA treatment resulted in saturation improvement from nadir of <84% to above 90% by 12 hours after exposure, with continued overall saturations >90-92% for the remainder of the study. Controls had severe oxygen saturation deterioration within hours of exposure, resulting in eventual death. As with blistering of the skin after mustard gas exposure, onset of respiratory distress is delayed. In these rats, even at this very high dose, onset of illness was delayed 6 hours, but some for 24 hours after exposure.

The individual pulse oximetry results from the rats treated with tPA after randomization (at the time of initial decrease of pOx to <85%), and receipt of the initial induction dose (show as time=0 on this graph) is shown in FIG. 18. Each subsequent vertical dotted line represents additional receipt of a maintenance tPA dose, every 4 hours. Here again the rats are tracked for the entire 48 hour period after exposure. All rats receiving tPA were >90% by 48 hours. One rat was rescued from 55% oxygen saturation back to 92% after tPA. All animals in this graph received their induction doses at different times after exposure, as previously stated, with a mean of 6 hours, but a few animals had their first dosing performed at 24-28 h post inhalation injury.

The clinical scores at euthanasia was determined (elective or at 48 hour study termination) in all study groups as shown in FIG. 19. Clinical distress was greatly improved after tPA treatment (tPA). Distress was monitored in rats after SM exposure (3.8 mg/kg) hourly for 48 hours. Combined clinical distress score encompassed respiratory distress (0-6) as well as activity (0-3), with a total score of 9 indicating maximal distress. SM exposure alone (NT), as well as placebo treatment (PBS) resulted in severe distress, while tPA treatment (tPA) minimized animal distress despite high dose SM inhalation. p<0.0001

The respiratory quality scores at euthanasia in all study groups was determined as shown in FIG. 20. The maximum (worst) score here is 6. Respiratory distress was greatly improved after tPA treatment (tPA), while controls (no treatment-NT; placebo PBS) had severe distress. p<0.0001

The total clinical distress scores was determined to trend over time×48 h after SM exposure in all three groups. Placebo treatment and non-treatment groups resulted in a sharp increase in clinical distress, with a maximum distress score of 9 in alive rats. tPA treated animals stabilized after receiving their induction tPA dose, and their distress plateaued at a minimal score of ~2 (out of 10) for the entire 48 hour experiment, with the receipt of maintenance tPA therapy every 4 hours (data not shown).

The arterial pH in naïve animals and all study groups at euthanasia was determined as shown in FIG. 21. Profound acidosis in the SM-exposed (non treatment-NT) and placebo-treated (PBS) animals was detected, while normal pH at euthanasia in tPA-treated animals (tPA) was detected. P<0.0001. The "Naïve" group represents air-breathing controls.

The arterial carbon dioxide tension ($paCO_2$, mm Hg) in naïve animals (air breathing controls) and all study groups at euthanasia was also determined as shown in FIG. 22. These were obtained invasively under anesthesia by aortic puncture. Marked hypercarbia in the SM-exposed (non treated-NT) and placebo-treated (PBS) animals was detected which is consistent with a severe ventilation defect. tPA treatment resulted in normal arterial $CO_2$ levels, corresponding to a normal ventilation response despite SM exposure. P<0.0001

The blood lactate in naïve animals (air breathing) and all study groups at euthanasia after exposure to 3.8 mg/kg SM was detected as shown in FIG. 23. There was a tendency for elevated lactate in all study groups. Elevation of blood lactate indicates suboptimal tissue oxygen delivery and suggests that the sick animals had both respiratory and metabolic acidosis. Notably, only rats in the tPA treatment group had lactate values comparable to air-breathing naïve controls ("Naïve").

The hematocrit values for naïve animals (air breathing) and the three SM-exposed groups (no treatment-NT, placebo treatment-PBS or the tPA treatment) was determined as shown in FIG. 24. Notably, hematocrits were not decreased in tPA-treated groups, suggesting that there was no blood loss in these animals.

Airway obstruction scores by fibrin casts in the three groups after mustard exposure were determined. Casts were revealed by airway microdissection after lung fixation (at euthanasia or 48 hours) of all major central lobar bronchi (5 lobes). These scores are obtained after microdissection of the trachea and all five lobes by morphometric study to quantitate the percent airway occlusion of each of the five main lobar bronchi by fibrin casts. These methods are described in Veress, L. A., et al. *American Journal of Respiratory Cell and Molecular Biology* 2013 48:4, 439-447. A score of 7 indicates 100% occlusion of all 5 main bronchi. The percent airway occlusion by cast was measured, then converted to a nominal score, weighted per ratio of lobar volume to total lung, then added for a composite score. SM-exposed (no treatment-NT) and placebo (PBS)-treated rats had scores exceeding 50% airway occlusion overall, while airway occlusion of main lobar bronchi in tPA-treated rats was negligible (score 4=50-65% total airway luminal occlusion). $p<0.0005$, ANOVA, Tukey's post-hoc analysis. Results are shown in FIG. 25.

Example 4

This example demonstrates the administration of a tPA analog, Reteplase (RETAVASE®), to animals who have been exposed to sulfur mustard (SM) vapor and that all indicators of airway obstruction, impaired gas exchange, oxygen delivery, and survival were improved in rPA treated animals as compared to untreated or vehicle-treated controls.

Methods

For retevase studies, rats were exposed to authentic sulfur mustard (SM) at Aberdeen Proving Grounds (Aberdeen, MD; USAMRICD). The exposure was to SM in an ethanolic vapor at a dose of 3.8 mg/kg inhaled (identical to doses used in tPA efficacy studies at the same site). Following exposures, four doses of rPA was given at 5 and 6 hours post exposure, then again at 10 and 11 hours post exposure. Each dose was 50 micro liters of agent given intratracheally, in liquid form, or vehicle (diluent for rPA). For the active agent (rPA), two concentrations were given, 0.05 units/kg and 0.10 units/kg of rPA. Animals were monitored continuously throughout a 12 hour study. Euthanasia criteria were utilized exactly as applied in the above tPA experiments. Animals surviving to 12 hours after SM exposure were then electively euthanized at the end of the 12 hour study period.

Results

The effect on survival with retevase (rPA) treatment as compared to various controls is shown in FIG. 26. Rats given no treatment (NT) succumbed by 12 hours. Rats treated with diluent only (diluent for rPA) had 20% survival (and 80% mortality) by 12 hours. By contrast, rats treated with rPA 0.05 unit/kg per dose, or with rPA 0.10 unit/kg per dose, showed survival rates >65% by 12 hours. Interestingly, the highest survival rate (75%) was in the group of rats given the lower dose of rPA (0.05 unit/kg/dose). These rPA doses are "tPA dose equivalent" doses in units/kg.

FIG. 27 reveals the effect of rPA on major airway cast scores at 12 hours after SM exposure. Cast scores for NT and diluent (vehicle, Veh) were both approximately 4, indicating that >50% of the total airway internal luminal areas were occluded. By contrast, mean major airway cast scores for both rPA dose groups were each less than half of this level and with the result for cast score for the lower dose of rPA being statistically significantly different from both control groups.

FIG. 28 illustrates the individual data for this same experiment, with circled data points indicating those animals that required early euthanasia (prior to 12 hour study termination).

The arterial blood pH values for rPA treated rats versus those of various control groups is shown in FIG. 29. Rats treated with the lower dose of rPA had arterial pH values that were significantly different from those of rats treated with vehicle (SM+Veh) or exposed to SM alone. The values for rats treated with the lower dose of rPA had arterial pH values comparable to those of naïve rats not exposed to sulfur mustard (i.e. >7.30). Well preserved (e.g. normal) arterial pH is another indicator of good cardiopulmonary function.

The arterial blood carbon dioxide content of rats treated with rPA versus those of 3 control groups is shown in FIG. 30. All rats in these studies, as in FIG. 17, were anesthetized prior to their blood being drawn. The principal finding here is that $paCO_2$ levels in arterial blood of rats treated with the lower dose of rPA were comparable to those of naïve rats not exposed to SM.

FIG. 31 reveals that rats treated with either dose of rPA had plasma bicarbonate (e.g. carbon dioxide contents) that were low and comparable to those of naïve rats.

The arterial blood oxygen content (partial pressure of oxygen; $p_aO_2$) of anesthetized animals at euthanasia is shown in FIG. 32. SM exposure caused a marked decline in this value compared to those of naïve animals. SM+Veh rats had comparable values for $p_aO_2$ as those seen in SM alone-exposed rats. By contrast, rats exposed to either dose of rPA after SM exposure had statistically improved values for $p_aO_2$ as compared to those for rats given SM or SM+Veh, and these values for rPA-treated rats were comparable to those seen in naïve rats.

FIG. 33 illustrates the individual and mean values for pulse oximetry (pOx, approximate arterial hemoglobin oxygen saturation in rats exposed to SM and given no treatment (NT), vehicle for rPA (Veh), or either of two doses of rPA. Although mean values for pOx were greater in either of the rPA-treated groups compared to either of these two control groups, and the means for the two treated groups were both 75% or greater, these values were certainly not normal. They were not as greatly improved, nor as consistently improved, at this level of SM exposure as seen after treatment for 12-48 hours with tPA.

It was noted that some animals in the retevase-treated groups, especially at higher doses, showed immediate respiratory distress following dosing with the rPA preparation. It was noted that these retevase (rPA) solutions appeared to be viscous and adhesive (sticky), especially at higher concentrations, and thus these solutions may have contributed to airway obstruction and respiratory distress, either due to direct mass effect and/or chemosensitivity. This may explain why rats treated with the lowest dose of rPA appeared to fare better than those treated with higher doses for some parameters.

The foregoing examples of the present invention have been presented for purposes of illustration and description. Furthermore, these examples are not intended to limit the invention to the form disclosed herein. Consequently, variations and modifications commensurate with the teachings of the description of the invention, and the skill or knowledge of the relevant art, are within the scope of the present invention. The specific embodiments described in the examples provided herein are intended to further explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

REFERENCES

1. Eisenmenger, W., Drasch, G., von Clarmann, M., Kretschmer, E., and Roider, G. 1991. Clinical and morphological findings on mustard gas [bis(2-chloroethyl) sulfide] poisoning. *J Forensic Sci* 36:1688-1698.
2. Willems, J. L. 1989. Clinical management of mustard gas casualties. *Ann Med Milit Belg* 3S:1-61.
3. Ghanei, M., Tazelaar, H. D., Chilosi, M., Harandi, A. A., Peyman, M., Akbari, H. M., Shamsaei, H., Bahadori, M., Aslani, J., and Mohammadi, A. 2008. An international collaborative pathologic study of surgical lung biopsies from mustard gas-exposed patients. *Respir Med* 102:825-830.
4. Watanabe, K., Ishida, T., Sugawara, A., Tachihara, M., and Munakata, M. 2008. An adult case of plastic bronchitis. *Intern Med* 47:1549.
5. Eberlein, M. H., Drummond, M. B., and Haponik, E. F. 2008. Plastic bronchitis: a management challenge. *Am J Med Sci* 335:163-169.
6. Goo, H. W., Jhang, W. K., Kim, Y. H., Ko, J. K., Park, I. S., Park, J. J., Yun, T. J., and Seo, D. M. 2008. CT findings of plastic bronchitis in children after a Fontan operation. *Pediatr Radiol* 38:989-993.
7. Do, T. B., Chu, J. M., Berdjis, F., and Anas, N. G. 2009. Fontan patient with plastic bronchitis treated successfully using aerosolized tissue plasminogen activator: a case report and review of the literature. *Pediatr Cardiol* 30:352-355.
8. Costello, J. M., Steinhorn, D., McColley, S., Gerber, M. E., and Kumar, S. P. 2002. Treatment of plastic bronchitis in a Fontan patient with tissue plasminogen activator: a case report and review of the literature. *Pediatrics* 109:e67.
9. Heath, L., Ling, S., Racz, J., Mane, G., Schmidt, L., Myers, J. L., Tsai, W. C., Caruthers, R. L., Hirsch, J. C., and Stringer, K. A. 2011. Prospective, longitudinal study of plastic bronchitis cast pathology and responsiveness to tissue plasminogen activator. *Pediatr Cardiol* 32:1182-1189.
10. Wakeham, M. K., Van Bergen, A. H., Torero, L. E., and Akhter, J. 2005. Long-term treatment of plastic bronchitis with aerosolized tissue plasminogen activator in a Fontan patient. *Pediatr Crit Care Med* 6:76-78.
11. Brogan, T. V., Finn, L. S., Pyskaty, D. J., Jr., Redding, G. J., Ricker, D., Inglis, A., and Gibson, R. L. 2002. Plastic bronchitis in children: a case series and review of the medical literature. *Pediatr Pulmonol* 34:482-487.
12. Seear, M., Hui, H., Magee, F., Bohn, D., and Cutz, E. 1997. Bronchial casts in children: a proposed classification based on nine cases and a review of the literature. *Am J Respir Crit Care Med* 155:364-370.
13. Tonan, M., Hashimoto, S., Kimura, A., Matsuyama, H., Kinose, H., Sawada, M., Shime, N., Tokuhira, N., Kato, Y., Sasaki, M., et al. 2011. Successful treatment of severe asthma-associated plastic bronchitis with extracorporeal membrane oxygenation. *J Anesth*.
14. Pawar, S. S., Chun, R. H., Rao, A. R., and Kerschner, J. E. 2011. Management of plastic bronchitis in a child with mild intermittent asthma. *Ann Otol Rhinol Laryngol* 120:697-699.
15. Mateos-Corral, D., Cutz, E., Solomon, M., and Ratjen, F. 2009. Plastic bronchitis as an unusual cause of mucus plugging in cystic fibrosis. *Pediatr Pulmonol* 44:939-940.
16. Waring, W. W., Brunt, C. H., and Hilman, B. C. 1967. Mucoid impaction of the bronchi in cystic fibrosis. *Pediatrics* 39:166-175.
17. Moser, C., Nussbaum, E., and Cooper, D. M. 2001. Plastic bronchitis and the role of bronchoscopy in the acute chest syndrome of sickle cell disease. *Chest* 120:608-613.
18. Deng, J., Zheng, Y., Li, C., Ma, Z., Wang, H., and Rubin, B. K. 2010. Plastic bronchitis in three children associated with 2009 influenza A(H1N1) virus infection. *Chest* 138:1486-1488.
19. Kuperman, T., Wexler, I.D., Shoseyov, D., Weintraub, M., Revel-Vilk, S., and Kerem, E. 2006. Plastic bronchitis caused by neoplastic infiltrates in a child. *Pediatr Pulmonol* 41:893-896.
20. Pruitt, B. A., Jr. 1974. Complications of thermal injury. *Clin Plast Surg* 1:667-691.
21. Cox, R. A., Burke, A. S., Soejima, K., Murakami, K., Katahira, J., Traber, L. D., Herndon, D. N., Schmalstieg, F. C., Traber, D. L., and Hawkins, H. K. 2003. Airway obstruction in sheep with burn and smoke inhalation injuries. *Am J Respir Cell Mol Riot* 29:295-302.
22. Veress, L. A., O'Neill, H. C., Hendry-Hofer, T. B., Loader, J. E., Rancourt, R. C., and White, C. W. 2010. Airway obstruction due to bronchial vascular injury after sulfur mustard analog inhalation. *Am J Respir Crit Care Med* 182:1352-1361.
23. Krenke, K., Krenke, R., Krauze, A., Lange, J., and Kulus, M. 2010. Plastic bronchitis: an unusual cause of atelectasis. *Respiration* 80:146-147.
24. Madsen, P., Shah, S. A., and Rubin, B. K. 2005. Plastic bronchitis: new insights and a classification scheme. *Paediatr Respir Rev* 6:292-300.
25. Zahorec, M., Kovacikova, L., Martanovic, P., Skrak, P., and Kunovsky, P. 2009. The use of high-frequency jet ventilation for removal of obstructing casts in patients with plastic bronchitis. *Pediatr Crit Care Med* 10:e34-36.
26. Wang, G., Wang, Y. J., Luo, F. M., Wang, L., Jiang, L. L., and Mao, B. 2006. Effective use of corticosteroids in treatment of plastic bronchitis with hemoptysis in Chinese adults. *Acta Pharmacol Sin* 27:1206-1212.
27. Shinkai, M., and Rubin, B. K. 2005. Macrolides and airway inflammation in children. *Paediatr Respir Rev* 6:227-235.
28. Haseyama, K., Satomi, G., Yasukochi, S., Matsui, H., Harada, Y., and Uchita, S. 2006. Pulmonary vasodilation therapy with sildenafil citrate in a patient with plastic bronchitis after the Fontan procedure for hypoplastic left heart syndrome. *J Thorac Cardiovasc Surg* 132:1232-1233.
29. Desai, M. H., Mlcak, R., Richardson, J., Nichols, R., and Herndon, D. N. 1998. Reduction in mortality in pediatric patients with inhalation injury with aerosolized heparin/N-acetylcystine [correction of acetylcystine] therapy. *J Burn Care Rehabil* 19:210-212.

30. Silva, R. C., Simons, J. P., Chi, D. H., Yellon, R. F., and Alper, C. M. 2011. Endoscopic treatment of plastic bronchitis. *Arch Otolaryngol Head Neck Surg* 137:401-403.
31. Wilson, J., Russell, J., Williams, W., and Benson, L. 2005. Fenestration of the Fontan circuit as treatment for plastic bronchitis. *Pediatr Cardiol* 26:717-719.
32. Shah, S. S., Drinkwater, D. C., and Christian, K. G. 2006. Plastic bronchitis: is thoracic duct ligation a real surgical option? *Ann Thorac Surg* 81:2281-2283.
33. Barber, B. J., Burch, G. H., Tripple, D., and Balaji, S. 2004. Resolution of plastic bronchitis with atrial pacing in a patient with fontan physiology. *Pediatr Cardiol* 25:73-76.
34. Laubisch, J. E., Green, D. M., Mogayzel, P. J., and Reid Thompson, W. 2011. Treatment of plastic bronchitis by orthotopic heart transplantation. *Pediatr Cardiol* 32:1193-1195.
35. Barreto, A. D., Alexandrov, A. V., Lyden, P., Lee, J., Martin-Schild, S., Shen, L., Wu, T. C., Sisson, A., Pandurengan, R., Chen, Z., et al. 2012. The argatroban and tissue-type plasminogen activator stroke study: final results of a pilot safety study. *Stroke* 43:770-775.
36. Kablau, M., Alonso, A., Hennerici, M. G., and Fatar, M. 2012. Treatment with tPA predicts better outcome even if MCA occlusion persists. *Int J Stroke*.
37. Fitchett, D. H., Theroux, P., Brophy, J. M., Cantor, W. J., Cox, J. L., Gupta, M., Kertland, H., Mehta, S. R., Welsh, R. C., and Goodman, S. G. 2011. Assessment and management of acute coronary syndromes (ACS): a Canadian perspective on current guideline-recommended treatment—part 2: ST-segment elevation myocardial infarction. *Can J Cardiol* 27 Suppl A:S402-412.
38. Zeltner, T. B., Bertacchini, M., Messerli, A., and Burri, P. H. 1990. Morphometric estimation of regional differences in the rat lung. *Exp Lung Res* 16:145-158.
39. Gao, X., Anderson, D. R., Brown, A. W., Lin, H., Amnuaysirikul, J., Chua, A. L., Holmes, W. W., and Ray, P. 2011. Pathological studies on the protective effect of a macrolide antibiotic, roxithromycin, against sulfur mustard inhalation toxicity in a rat model. *Toxicol Pathol* 39:1056-1064.
40. Fairhall, S. J., Jugg, B. J., Read, R. W., Stubbs, S. J., Rutter, S. J., Smith, A. J., Mann, T. M., Jenner, J., and Sciuto, A. M. 2010. Exposure-response effects of inhaled sulfur mustard in a large porcine model: a 6-h study. *Inhal Toxicol* 22:1135-1143.
41. O'Neill, H. C., Orlicky, D. J., Hendry-Hofer, T. B., Loader, J. E., Day, B. J., and White, C. W. 2011. Role of reactive oxygen and nitrogen species in olfactory epithelial injury by the sulfur mustard analogue 2-chloroethyl ethyl sulfide. *Am J Respir Cell Mol Biol* 45:323-331.
42. 1993. The effects of tissue plasminogen activator, streptokinase, or both on coronary-artery patency, ventricular function, and survival after acute myocardial infarction. The GUSTO Angiographic Investigators. *N Engl J Med* 329:1615-1622.
43. Lansberg, M. G., O'Donnell, M. J., Khatri, P., Lang, E. S., Nguyen-Huynh, M. N., Schwartz, N. E., Sonnenberg, F. A., Schulman, S., Vandvik, P. O., Spencer, F. A., et al. 2012. Antithrombotic and Thrombolytic Therapy for Ischemic Stroke: Antithrombotic Therapy and Prevention of Thrombosis, 9th ed: American College of Chest Physicians Evidence-Based Clinical Practice Guidelines. *Chest* 141:e6015-6365.
44. Kearon, C., Aid, E. A., Comerota, A. J., Prandoni, P., Bounameaux, H., Goldhaber, S. Z., Nelson, M. E., Wells, P. S., Gould, M. K., Dentali, F., et al. 2012. Antithrombotic therapy for VTE disease: Antithrombotic Therapy and Prevention of Thrombosis, 9th ed: American College of Chest Physicians Evidence-Based Clinical Practice Guidelines. *Chest* 141:e419S-494S.
45. Hilleman, D., and Campbell, J. 2011. Efficacy, safety, and cost of thrombolytic agents for the management of dysfunctional hemodialysis catheters: a systematic review. *Pharmacotherapy* 31:1031-1040.
46. Garcia, A., Gander, J. W., Gross, E. R., Reichstein, A., Sheth, S. S., Stolar, C. J., and Middlesworth, W. 2011. The use of recombinant tissue-type plasminogen activator in a newborn with an intracardiac thrombus developed during extracorporeal membrane oxygenation. *J Pediatr Surg* 46:2021-2024.
47. Rahman, N. M., Maskell, N. A., West, A., Teoh, R., Arnold, A., Mackinlay, C., Peckham, D., Davies, C. W., Ali, N., Kinnear, W., et al. 2011. Intrapleural use of tissue plasminogen activator and DNase in pleural infection. *N Engl J Med* 365:518-526.
48. Johnson, A. R., Jensen, H. L., Peltier, G., and DelaCruz, E. 2011. Efficacy of intravenous tissue plasminogen activator in frostbite patients and presentation of a treatment protocol for frostbite patients. *Foot Ankle Spec* 4:344-348.
49. van Goor, H., Bom, V. J., van der Meer, J., Sluiter, W. J., Geerards, S., van der Schaaf, W., de Graaf, J. S., and Bleichrodt, R. P. 1996. Pharmacokinetics of human recombinant tissue-type plasminogen activator, administered intra-abdominally, in a rat peritonitis model. *Eur Surg Res* 28:287-294.
50. Enkhbaatar, P., Murakami, K., Cox, R., Westphal, M., Morita, N., Brantley, K., Burke, A., Hawkins, H., Schmalstieg, F., Traber, L., et al. 2004. Aerosolized tissue plasminogen inhibitor improves pulmonary function in sheep with burn and smoke inhalation. *Shock* 22:70-75.

What is claimed is:

1. A method to increase the survival of a subject having been exposed to sulfur mustard (SM) or an analog thereof, wherein exposure to the SM or an analog thereof results in fibrin-containing cast formation in the airways of the subject, comprising administering to the airway of the subject tissue plasminogen activator (tPA) or analog thereof, wherein survival of the subject is increased.

2. The method of claim 1, wherein the analog is 2-chloroethyl ethylsulfide (CEES).

3. The method of claim 1, wherein the tPA is administered in a dose amount of about 0.1 mg/kg/dose to about 1.0 mg/kg/dose.

4. The method of claim 1, wherein the tPA is administered in a dose amount of about 0.4 mg/kg/dose to about 0.8 mg/kg/dose.

5. The method of claim 1, wherein the tPA is administered to the airway of the subject by a delivery method selected from the group consisting of inhalation, nebulization, aerosolization and intratracheal delivery.

6. The method of claim 1, wherein the step of administering comprises administering to the subject an initial dose of the tPA followed by administering an additional dose of the tPA to the subject.

7. The method of claim 1, wherein the step of administering the tPA is conducted immediately after exposure of the subject to the SM or analog thereof.

8. The method of claim 1, wherein the step of administering the tPA is conducted within about 0 hours to about 14 days after exposure of the subject to the SM or analog thereof.

9. The method of claim 1, wherein the step of administering the tPA comprises administering an initial dose of the tPA following exposure of the subject to the SM or analog thereof and administering at least one additional dose of the fibrinolytic agent after the administration of the initial dose of the tPA.

10. The method of claim 9, wherein the step of administering the at least one additional dose is conducted about 30 minutes to about 60 minutes after the administration of the initial dose.

11. The method of claim 10, wherein the step of administering the at least one additional dose is repeated.

12. The method of claim 11, wherein the step of administering the at least one additional dose is repeated about every 4 hours to about every 6 hours.

13. The method of claim 1, wherein the subject is human.

* * * * *